United States Patent [19]

Jelenkovic et al.

[11] Patent Number: 6,072,105
[45] Date of Patent: Jun. 6, 2000

[54] INSECT-RESISTANT TRANSGENIC EGGPLANT AND METHOD OF MAKING

[75] Inventors: Gojko Jelenkovic, Piscataway; Sharon Billings, Middletown, both of N.J.

[73] Assignee: Rutgers, The State University of New Jersey, New Brunswick, N.J.

[21] Appl. No.: 08/920,270

[22] Filed: Aug. 22, 1997

Related U.S. Application Data

[60] Provisional application No. 60/024,544, Aug. 23, 1996.

[51] Int. Cl.$^7$ ............................... A01H 5/00; A01H 5/10
[52] U.S. Cl. ........................................................ 800/317
[58] Field of Search ...................... 536/23.71; 435/172.3, 435/320.1, 69.1, 419, 468; 800/205, 250, DIG. 40, 279, 301, 317

[56] References Cited

U.S. PATENT DOCUMENTS 5,240,839   8/1993   Serres et al. ........................ 435/172.3

OTHER PUBLICATIONS

Marc DeBlock, The Cell Biology of Plant Transformation: Current State, Problems Prospects and the Implications for Plant Breeding. Euphytica 71: 1–14, 1993.

R.M.Gosukonda, C.S.Prakesh and A.P. Dessai. Shoot Regeneration in Vitro from Diverse Genotypes of Sweetpotato and Multiple Shoot Production per Explant. HortScience 30: 1074–1077, 1995.

N.J. Shackleford, C.A. Chlan. Identification of Antibiotics that are Effective in Eliminating *Agrobacterium tumefaciens*. Abstract—Plant Mol. Biol. Rep. 14: 50–7, 1996.

A. Sultana, P.S. Ahuja. Cephalexin—A Better Alternative to Cefotaxime in Plant Genetic Transformation Experiments. Abstract—Indian J. Exp. Biol. 31: 1993.

E.R. Ward and W.M. Barnes. Integration of Multiple Copies of a Foreign Sequence into the Ti Plasmid of *Agrobacterium tumefaciens*. Gene 75: 305–314, 1989.

J.M. Wierenga, D.L. Norris and M.E. Whalon. Stage–Specific Mortality of Colorado Potato Beetle (Coleoptera: Chrysomelidae) Feeding on Transgenic Potatoes. J. Economic Entomology 89: 1047–1052, 1996.

Adang, M.J., M.S. Brody, G. Cardineau, N. Eagan, R.T. Roush, C.K. Shewmaker, A. Jones, J.V. Oakes, and K.E. McBride. 1993. The reconstruction and expression of a *Bacillus thuringiensis cryIIIA* gene in protoplasts and potato plants. Plant Mol. Biol. 21:1131–1145.

Armstrong, C.L., G.B. Parker, J.C. Pershing, S.M. Brown, P.R. Sanders, D.R. Duncan, T. Stone, D.A. Dean, D.L. DeBoer, J. Hart, A.R. Howe, F.M. Morrish, M.E. Pajeau, W.L. Petersen, B.J. Reich, R. Rodriguez, C.G. Santino, S.J. Sato, W. Schuler, S.R. Sims, S. Stehling, L.J. Tarochione, and M.E. Fromm. 1995. Field evaluation of European corn borer control in progeny of 173 transgenic corn events expressing an insecticidal protein from *Bacillus thuringiensis*. Crop Sci. 35:550–557.

(List continued on next page.)

*Primary Examiner*—Lynette R. F. Smith
*Assistant Examiner*—Amy J. Nelson
*Attorney, Agent, or Firm*—Dann, Dorfman, Herrell and Skillman

[57] ABSTRACT

Transgenic eggplants (*Solanum melongena* L.) are provided, along with improved culture media and methods enabling efficient regeneration of shoots from cultured explants. The regeneration media contain a combination of growth factors that significantly increase the efficiency of shoot regeneration. Selection media contain combinations of antibiotics particularly effective in supporting shoot regeneration and eliminating Agrobacterium from explants transformed via tDNA techniques. The invention also provides a transgenic eggplant comprising a Bt gene modified for expression in plants. These transgenic eggplants demonstrate significant resistance to the Colorado potato beetle in the greenhouse and in the field.

3 Claims, 9 Drawing Sheets

OTHER PUBLICATIONS

Billings, S., G. Jelenkovic, C.-K. Chin, and J. Eberhardt. 1997. The effect of growth regulators and antibiotics on eggplant transformation. J. Amer. Soc. Hort. Sci. 122:158–162.

Chen, Q., G. Jelenkovic, C.-K. Chin, S. Billings, J. Eberhardt, J.C. Goffreda, and P. Day. 1995. Transfer and transcriptional expression of coleopteran cryIIIB endotoxin gene of *Bacillus thuringiensis* in eggplant. J. Amer. Sco. Hort. Sci. 120:921–927.

Guri, A. and K.C. Sink. 1988. Agrobacterium transformation of eggplant. J. Plant Physiol. 133:52–55.

Jefferson, R.A. 1987. Assaying chimeric genes in plants: the GUS gene fusion system. Plant Mol. Biol. Rpt. 5:387–405.

Koziel, M.G., G.L Beland, C. Bowman, N.B. Carozzi, R. Crenshaw, L. Crossland, J. Dawson, N. Desai, M. Hill, S. Kadwell, K. Launis, K. Lewis, D. Maddox, K. McPherson, M. Meghji, E. Merlin, R. Rhodes, G. Warren, M. Wright, and S.V. Evola. 1993. Field performance of elite transgenic maize plants expressing an insecticidal protein derived from *Bacillus thuringiensis*. Bio/Technology 11:194–200.

Lodge, J.K., K. Wojciech, and N. Turner. 1995. Broad–spectrum virus resistance in transgenic plants expressing pokeweed antiviral protein. Proc. Natl. Acad. Sci. USA 90:7089–7093.

McCormick, S., J. Niedermeyer, J. Fry, A. Barnason, R. Horsch, and R. Fraley. 1986. Leaf disc transformation of cultivated tomato (*L. esculentum*) using *A. tumefaciens*. Plant Cell Rpt. 5:81–84.

Mittler, R., V. Shulaev and E. Lam. 1995. Coordinated activation of programmed cell death and defense mechanisms in transgenic tobacco plants expressing a bacterial proton pump. The Plant Cell 7:29–42.

Perlak, F.J., R.W. Deaton, T.A. Armstrong, R.L. Fuchs, S.R. Sims, J.T. Greenplate, and D.A. Fischhoff. 1990. Insect resistant cotton plants. Bio/Technology 8:939–943.

Perlak, F.J., R.L. Fuchs, D.A. Dean, S.L. McPherson, and D.A. Fischhoff. 1991. Modification of the coding sequence enhances plant expression of insect control protein genes. Proc. Natl. Acad. Sci. USA 88:3324–3328.

Sutton, D.W., P.K. Havstad, and J.D. Kemp. 1992. Synthetic cryIIIA gene from *Bacillus thuringiensis* improved for high expression in plants. Transgenic Res. 1:228–236.

van der Salm, T., D. Bosch, G. Honée, L. Feng, E. Munsterman, P. Bakker, W.J. Stiekema, and B. Visser. 1994. Insect resistance of transgenic plants that express modified *Bacillus thruingiensis cryIA* ( *b* ) and cryIC genes: a resistance management strategy. Plant Mol. Biol. 26:51–59.

Wang, C., C.-K. Chin, and A. Chen. In Press. Expression of the yeast delta −9 desaturase gene in tomato enhances its resistance to powdery mildew. Physiol. Mol. Plant Path.

Wu, G., B. Short, E. Lawrence, E. Levine, K. Fitzsimmons, and D. Shah. 1995. Disease resistance conferred by expression of a gene encoding $H_2O_2$–generating glucose oxidase in transgenic potato plants. The Plant Cell 7:1357–1368.

Wunn, J., A. Kloti, P.K. Burkhardt, G.C.G. Biswas, K. Launis, V.A. Iglesias, and I. Potrykus. 1996. Transgenic indica rice breeding line IR58 expressing a synthetic cryIA(b) gene from *Bacillus thuringiensis* provides effective insect pest control. Bio/Technology 14:171–176.

Chen Q, et al. "Transfer and transcriptional expression of coleopteran cryIIIB endotoxin gene of *Bacillus thuringiensis* in eggplant." J. Amer. Soc. Hort. Soc. 120: 921–927, Nov. 1995.

Sutton DW, et al. "Synthetic cryIIIA gene from *Bacillus thuringiensis* improves for high expression in plants." Transgenic Res. 1: 228–236, 1992.

Guri A, et al. "Agrobacterium transformation of eggplant." J.Plant Physiol. 133: 52–55, 1988.

Rotino GL, et al. Transformation of eggplant (*Solanum melongena L.*) Plant Cell Rep. 9: 26–29, 1990.

O'Brien MJ, et al. "Evaluation of eggplant accessions and cultivars for resistance to Verticillium wilt." Plant Dis. 67: 763–764, 1983.

Koziel MG, et al. "The insecticidal crystal proteins of *Bacillus thuringiensis*: Past, present and future uses." Biotech. Genet. Engineer. Rev. 11: 171–228, Dec. 1993.

Kb 2.3
2

6.5

4.3

SEQUENCE LISTING

<160> NUMBER OF SEQ ID NOS: 1

<210> SEQ ID NO 1
<211> LENGTH: 1794
<212> TYPE: DNA
<213> ORGANISM: Artificial Sequence
<220> FEATURE:
<223> OTHER INFORMATION: /note = synthetic construct

<400> SEQUENCE: 1
atgactgctg ataacaacac ggaggcactt gatagctcta ccaccaagga tgtcattcaa 60
aagggcattt ccgtggtggg tgatctcctt ggcgtcgttg gattcccctt cggtggagcc 120
cttgtttcct tctacaccaa cttcctcaac actatttggc caagcgagga cccctggaag 180
gccttcatgg agcaagtgga ggcactgatg gatcagaaga ttgccgatta cgcaaagaac 240
aaggcccttg cagagctgca aggccttcaa aacaatgtcg aggattatgt tagcgcactc 300
agctcatggc aaaagaaccc tgtgagctca cgtaacccac acagccaggg tcgtattaga 360
gagctgttct ctcaagcaga gagccatttc cgtaactcaa tgccttcctt tgcaatttct 420
ggatacgagg ttctcttcct caccacttac gcacaagctg ccaacacgca cctcttcttg 480
cttaaggacg cacaaatcta cggagaggag tggggatacg agaaggagga tattgccgag 540
ttctacaaga gacaacttaa acttacgcaa gagtacactg atcactgtgt caagtggtac 600
aacgttggac ttgataaact cagaggttca tcttacgagt cttgggtgaa cttcaaccgt 660
tatcgcagag agatgaccct taccgtgcta gatctcatcg cactgttccc actgtacgat 720

-continued

```
gttcgtcttt acccaaagga ggttaagacc gagcttacca gagacgttct caccgatcca    780
attgtcggag tcaacaacct tagaggctac ggaaccacct tctctaatat tgagaactac    840
attcgcaagc cacacctgtt tgactacctg cacagaatcc aattccacac gcgtttccaa    900
ccaggatact acggtaacga ctctttcaac tactggtccg gaaactacgt ttcaactaga    960
ccaagcatag gatcaaacga tattatcacc tctccattct acggaaacaa gtccagcgag   1020
cctgtgcaaa accttgagtt caacggagag aaggtctaca gagccgtggc aaacaccaac   1080
cttgccgtct ggccctccgc agtgtactca ggtgttacca aagtggagtt cagccaatac   1140
aacgatcaaa ccgatgaggc aagcactcaa acgtacgact caaagagaaa cgttggcgcc   1200
gtcagctggg attctatcga tcaattgcct ccagagacca ccgatgagcc tcttgagaag   1260
ggatacagcc accaactcaa ctacgtgatg tgcttcttga tgcagggtag cagaggaacc   1320
atcccagtgc tcacttggac ccacaagagc gtggacttct tcaacatgat tgattccaag   1380
aagattaccc aacttccctt ggtgaaggca tacaagctcc aatctggtgc ctccgttgtc   1440
gcaggtccta ggttcaccgg aggagatatc attcagtgca ccgagaacgg aagcgccgca   1500
actatctacg ttaccccctga tgtgtcctac tctcaaaagt accgcgccag aattcactac   1560
gcctctacct ctcagattac cttcacgctc agcttggacg gagcaccctt caaccaatac   1620
tacttcgata agacgattaa caagggagac acccttacgt acaactcatt caaccttgct   1680
agcttcagca ccccattcga gttgtcaggc aacaacctcc aaattggcgt caccggactt   1740
agcgccggag ataaggtcta catagacaag attgagttca ttccagtgaa ttaa         1794
```

INSECT-RESISTANT TRANSGENIC EGGPLANT AND METHOD OF MAKING

This application claims priority to U.S. Provisional Application Ser. No. 60/024,544, filed Aug. 23, 1996.

FIELD OF THE INVENTION

This invention relates to the field of plant breeding, insect resistance and plant transformation methods. More specifically, an improved method of generating transgenic eggplants is provided, and a transgenic, insect-resistant eggplant is provided, produced by the improved methods.

BACKGROUND OF THE INVENTION

Various scientific and scholarly articles are referred to in parentheses throughout the specification. These articles are incorporated by reference herein to describe the state of the art to which this invention pertains. Full citations of the references appear at the end of the specification.

Eggplant (*Solanum melongena* L.) is an important crop species in Europe, Asia and North America. However, in some parts of the world its commercial production is frequently hampered by devastating attacks by the Colorado potato beetle (CPB, *Leptinotarsa decemlineata* [Say]). In the absence of an effective pest control program, the CPB may cause total destruction of eggplant crops. Chemical pesticide application is costly to farmers and damaging to the environment.

Attempts have been made to produce eggplant resistant to the CPB. For instance, the native cryIIIB *Bacillus thuringiensis* gene was used for transformation of eggplant (Chen et al., 1995). The native cryIIIB gene encodes a protein in spores of *Bacillus thuringiensis* (Bt) which is toxic to certain coleopteran insects, including CPB. A transfer of this cryIIIB gene via the recombinant DNA approach was expected to produce sufficient amounts of toxic protein in eggplants to provide an adequate level of resistance to CPB. However, field tests of more than 200 primary transgenic eggplants and their $R_1$ progeny containing the cryIIIB gene failed to demonstrate any noticeable resistance to the CPB. It appears that this gene was poorly expressed when incorporated into eggplant. The experimental evidence suggests that the transcription process of the native Bt genes in certain plant cells generates fragmented mRNA, instead of entire transcripts, which is non-functional in the translation process (Murray et al., 1991; Van Aarssen et al., 1995). In these instances the lack of CPB resistance in transgenic plants is directly related to the absence of toxic protein synthesis in the cells.

Analysis of the coding sequences of a number of native Bt genes has revealed structural features not found in most plant genes (Perlak et al., 1991; Sutton et al., 1992; Adang et al., 1993). For instance, along the coding region of the native Bt gene, there are frequent stretches of multiple A's and T's. In addition, the GC content of the native Bt gene is much lower than in plant genes. The polyadenylation signal sequence AATAAA of plant genes and the mRNA destabilizing ATTTA sequence is often found in the middle of the coding region. Also, the codon usage of the native Bt gene is different from many plant genes.

Modification of sequences in the native Bt genes by nucleotide substitution has been undertaken with the goal of making the Bt coding sequence more similar to plant gene coding sequences. Perlak modified the lepidopteran cryIA (b) and cryIA(c) Bt genes by changing 3% and 20%, respectively, of the nucleotides (Perlak et al., 1990; Perlak et al., 1991). In comparison to the corresponding native genes, the toxic protein production from the synthetic Bt genes in transgenic cotton and tomato was increased. Modified versions of the coleopteran cryIIIA gene have been engineered by Sutton et al. (1992) and Adang et al. (1993) who changed the coding sequence by 17% and 11% respectively. The modified genes enhanced production of the toxic protein in tobacco (Sutton et al., 1992) and potato cells (Adang et al., 1993), enhancing their resistance to a representative insect pest.

Recently, it has been reported that modified cryIA(b) and cryIC genes were highly expressed in tomato (van der Salm et al., 1994), syn cryIA in corn (Armstrong et al., 1995), and syn cryIA(b) in rice (Wunn et al., 1996). These results convincingly demonstrated that recovery of a high level of pest resistance in plants could be achieved by using modified Bt genes rather than native ones.

Transfer of genetic information into the genome of a plant species by recombinant DNA techniques has become an important strategy in basic studies of plant biology as well as in the improvement of cultivated plants. However, a severe impediment to the applicability of this approach with many plant species is the inefficacy of a reliable transformation and regeneration procedure in vitro. A review (Van Wordragen and Dons, 1992) describes *Agrobacterium tumefaciens*-mediated transformation of plant species, still the most widely used transfer system in plants, and indicates that only a few species (model plant species) can be transformed and regenerated routinely with commonly used procedures. The great majority of plants, the so-called recalcitrant species, require empirical development of a particular transformation protocol for a particular species. In developing such species-specific transformation protocols, efficiency is an important attribute in evaluating various protocols. This is of particular importance in cases where it is necessary to secure a large population of transformed genotypes for subsequent screening and selection of desired traits.

Eggplant is a species that has been recalcitrant to transformation. Rotino and Gleddie (1990) reported a transformation efficiency of only seven percent. Neither those methods, nor the methods of Guri and Sink (1988) have been demonstrated to result in transformation efficiencies greater than 7%. Thus, improved methods are needed for high efficiency transformation of eggplant, especially with useful genes, such as cryIIIA and other genes suitable for expression in plants, for the purpose of generating transgenic varieties that are resistant to insects or other plant pathogens.

SUMMARY OF THE INVENTION

This invention provides improved methods and culture media for generating transgenic eggplants. A transgenic, insect-resistant eggplant is also provided, produced by the improved methods.

According to one aspect of the invention, regeneration medium for regenerating shoots of *Solanum melongena* from tissue explants. The regeneration medium comprises a plant tissue culture medium that includes between about 0.01 and 1.0 μm thidiazuron and between about 5 and 20 μm $N^6$-[isopentyl] adenine.

According to another aspect of the invention, selective regeneration medium (also referred to as a selection medium) is provided for regenerating shoots of *Solanum melongena* from tissue explants transformed with a DNA construct that confers kanamycin resistance to the transformed tissue explants. This medium comprises a plant tissue culture medium that includes between about 0.01 and 1.0 μm thidiazuron, between about 5 and 20 μm N$^6$-[isopentyl] adenine and between about 40 and 70 μg/mL kanamycin. When the explants are transformed by an Agrobacterium-mediated transformation protocol, the selection medium further comprises an antibiotic for elimination of the Agrobacterium, preferably augmentin or cefotaxime, and most preferably at between about 150 and 300 μg/mL augmentin or about 500 μg/mL cefotaxime.

According to another aspect of the invention, a method for regenerating shoots of *Solanum melongena* from tissue explants is provided. The method comprises culturing the tissue explants on a regeneration medium comprising a plant tissue culture medium that includes between about 0.01 and 1.0 μm thidiazuron and between about 5 and 20 μm N$^6$-[isopentyl] adenine.

According to another aspect of the invention, a method is provided for selectively regenerating shoots of *Solanum melongena* from tissue explants suspected to be transformed with a DNA construct that confers kanamycin resistance. This method comprises: (a) culturing the tissue explants on a regeneration medium comprising a plant tissue culture medium that includes between about 0.01 and 1.0 μm thidiazuron and between about 5 and 20 μm N$^6$-[isopentyl] adenine; and (b) transferring the cultured explants to a selection medium comprising the regeneration medium which further comprises between about 40 and 70 μm kanamycin, whereupon the transformed explants, if any, regenerate shoots. In cases where the explants are subjected to Agrobacterium-mediated transformation, the selection medium further comprises an antibiotic for elimination of Agrobacterium.

According to yet another aspect of the invention, method of making a transgenic eggplant having a cryIIIA gene is provided. This method includes the following steps: (a) pre-culturing tissue explants (preferably leaf explants) of the eggplant on a regeneration medium comprising a plant tissue culture medium that includes between about 0.01 and 1.0 μm thidiazuron and between about 5 and 20 μm N$^6$-[isopentyl] adenine; (b) inoculating the explants with an Agrobacterium carrying a recombinant DNA comprising the cryIA gene and a selectable marker gene that confers kanamycin resistance to cells transformed with the recombinant DNA; (c) post-culturing the inoculated explants on the regeneration medium for a time sufficient to enable the Agrobacterium to transform cells of the explants; (d) selectively culturing the post-cultured explants on a selection medium comprising the regeneration medium supplemented with about 40–70 μg/mL kanamycin and an antibiotic for eliminating Agrobacterium selected from the group consisting of about 150–300 μg/mL augmentin and about 500 μg/mL cefotaxime, for a time sufficient to enable shoot formation from said explants, said selective culturing resulting in formation of shoots from cells transformed with the recombinant DNA comprising the cryIIIA gene; and (e) regenerating cryIIIA transgenic eggplants from the transformed shoots.

According to yet another aspect of the invention, a transgenic eggplant produced by the foregoing method is provided. In a preferred embodiment, the transgenic eggplant is *Solanum melongena* L. cv. Hibush. Particularly preferred is the genotype 55-30, from which seeds have been produced.

According to yet another aspect of the invention, transgenic eggplant comprising a *Bacillus thuringiensis* gene modified for expression in plants is provided. The gene produces an amount of a Bt insecticidal protein sufficient to render the eggplant resistant to an insect pest that is sensitive to the Bt insecticidal protein. In a preferred embodiment, the gene is a modified *Bacillus thuringiensis* var. *tenebrionis* gene and the insect pest is a coleopteran insect. Most preferably, the gene is a cryIIIA gene and the insect is Colorado potato beetle.

According to yet another aspect of the invention, a transgenic eggplant comprising a synthetic cryIIIA gene is provided. Preferably, the eggplant is *Solanum melongena* L. cv. Hibush, and most preferably genotype 55-30, seeds of which have been produced.

BRIEF DESCRIPTION OF THE DRAWINGS

FIG. 5A: the syn cryIIIA gene under control of 35S promoter and NOS polyadenylation sequence inserted at the Hind III site in pBI121. FIG. 5B: Hind III restriction of genomic DNA from 13 transgenic plants and one control. Each phenotypic group is represented: Lanes 1–4, G+R+; lane 5, G−R−; lanes 6–9, G+R+; lanes 10–11, G+R−, lanes 12–13, G−R+; lane 14, control. Plant DNA was probed with a DNA DIG-labeled 1.8 Kb syn cryIIIA fragment. FIG. 5C: Hind III restriction of plant DNA, same order as above, but probed with a DNA DIG-labeled 1.8 Kb uidA fragment.

FIG. 6A: RNA of 13 transformants and 1 control (Lanes 1–4, G+R+; lane 5, G−R−; lanes 6–9, G+R+; lanes 10–11, G+R−, lanes 12–13, G−R+; lane 14, control), probed with a DNA DIG-labeled syn cryIIIA fragment. FIG. 6B: RNA of the same 14 genotypes probed with a DNA DIG-labeled uidA fragment.

FIGS. 7A–7B. Southern blot analysis of 33 R$_1$ seedling offspring of transgenic genotype Btt25a. FIG. 7A: Hind III restriction of genomic DNA probed with a DNA DIG-labeled 1.8 Kb syn cryIIIA fragment. The segregation of syn cryIIIA follows a duplicate gene ratio of 15:1. FIG. 7B: Hind III restriction of genomic DNA probed with a DNA DIG-labeled 1.8 Kb uidA fragment. Segregation of the uidA demonstrates a dihybrid segregation ratio of 9:3:3:1. Lane 1 is DIG-labeled DNA marker; the next 33 lanes are individual seedling offspring of Btt25a. Lane sequence is the same for both A and B.

DETAILED DESCRIPTION OF THE INVENTION

Figure 1:
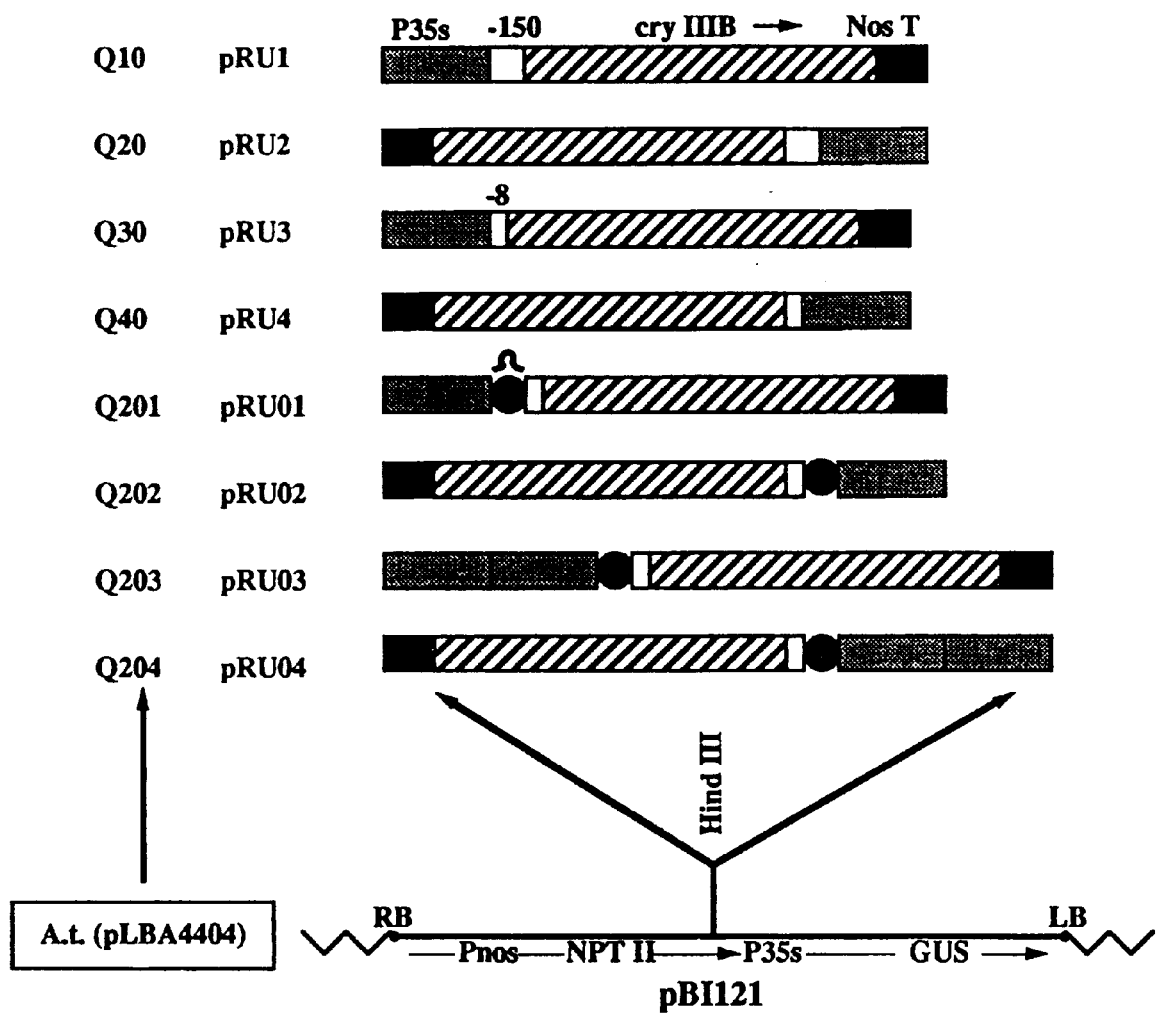
FIG. 1. "Q Series." Plasmid constructs pRU1–pRU04 ligated into pBI121 at Hind III restriction site, producing new *Agrobacterium tumefaciens* strains Q10–Q204.

The present invention provides a method for generating transgenic eggplants that is superior to other methods heretofore available. The protocol uses leaves or stems of in vitro-grown seedlings as a source of explants and a tissue culture method for transformation. The regeneration protocol is particularly important for producing transgenic eggplants and is statistically much more productive than prior methods. The medium used for shoot regeneration is believed to be the most important factor for the success of the transformation protocol provided in accordance with the invention. It will be appreciated by those of skill in the art, however, that the shoot regeneration medium described herein can be used for efficiently regenerating eggplant shoots from explants regardless of whether they have been transformed with a foreign gene of interest.

It has been discovered that a particular combination of growth factors in the shoot regeneration ("SR") medium significantly enhances shoot regeneration, thereby improving the efficiency of the regeneration. The growth regulatory factors comprise a combination of thidiazuron (TDZ) and $N^6$-[isopentyl] adenine (2iP). The medium is prepared using a standard plant tissue culture medium into which is dispersed the appropriate amounts of TDZ and 2iP. In a preferred embodiment, Murashige-Skoog (MS) salts are used, supplemented with a vitamin mix, sucrose and agar (liquid culture medium does not contain agar) at a preferable final pH of about 5.7–5.9. MS salts are commercially available (Gibco BRL), or can be prepared according to the following proportions: 20.6 mM $NH_4NO_3$; 18.8 mM $KNO_3$; 3.0 mM $CaCl_2.2H_2O$; 1.5 mM $MgSO_4.7H_2O$; 1.2 mM $KH_2PO_4$; 5 $\mu$M KI; 0.1 mM $H_3BO_3$, 0.1 mM $MnSO_4.4H_2O$; 30 $\mu$M $ZnSO_4.7H_2O$; 1.0 $\mu$M $Na_2MoO_4.2H_2O$; 0.1 $\mu$M $CuSO_4.5H_2O$; 0.1 $\mu$M $CoCl_2.6H_2O$; 0.1 mM Fe-Versenate (EDTA). MS vitamins can be purchased (Sigma) or can be prepared according to the following proportions: 100 mg/L inositol; 0.5 mg/L nicotinic acid; 0.5 mg/L pyridoxine HCl; 0.1 mg/L thiamine HCl. The medium also contains an appropriate carbon source, e.g., sucrose (2%), and agar for semi-solid media (0.5–0.6% is preferable).

For selection of transformed tissue, a selection medium comprising the aforementioned SR medium and appropriate antibiotics is used. The choice and concentration of antibiotics in the selection medium is also important to the success of the regeneration protocol. In transformation protocols based on kanamycin resistance as the selectable marker, kanamycin is used as the antibiotic, but at lower concentration than used in previous methods. Depending on the selectable marker gene used in the transformation protocol (e.g., BAR, ALS), antibiotics other than kanamycin would be used in the selection medium. If the transformation protocol is an Agrobacterium-mediated transformation, an antibiotic to eliminate Agrobacterium is included in the selection medium. Augmentin is the preferred antibiotic for this purpose. Augmentin is prepared, e.g. as a 4 mg/mL stock, by adding 300 mg amoxicillin (Sigma) to 100 ml of tepid water (e.g. 37° C.), dissolving the amoxicillin, then adding 75 mg lithium clavulanate (Beecham), followed by filter sterilization. Cefotaxime has also been found effective for eliminating Agrobacterium.

In a preferred embodiment, the SR culture medium is prepared in MS salts/vitamins with sucrose and agar (as described above) and contains between about 0.01 and 1.0 $\mu$M (most preferably 0.1 $\mu$M) TDZ in combination with about 5–20 $\mu$M (preferably 20 $\mu$M) 2iP. The addition of TDZ significantly improves regeneration efficiency, as described in greater detail in Example 1 below. In a preferred embodiment comprising Agrobacterium-mediated transformation and selection by kanamycin resistance, kanamycin at about 40–70 $\mu$g/mL (preferably 40–50 $\mu$g/mL) has been found to be most effective in selecting for transgenic buds and shoots. Augmentin at about 150–300 $\mu$g/mL (preferably 300 $\mu$g/mL) is used for *Agrobacterium tumefaciens* elimination, and also has been found to enhance shoot proliferation. In an alternative embodiment, cefotaxime (preferably about 500 $\mu$g/mL) is used.

When used herein in describing components of media or other experimental results, the term "about" means within a margin of commonly acceptable error for the determination being made, using standard methods. For tissue culture media in particular, persons skilled in the art would appreciate that the concentrations of various components initially added to culture media may change somewhat during use of the media, e.g., by evaporation of liquid from the medium or by condensation onto the medium. Moreover, it is understood that the precise concentrations of the macronutrients, vitamins and carbon sources are less critical to the efficacy of the media than are the micronutrient, hormone and antibiotic concentrations.

Agrobacterium-mediated transformation is exemplified herein for transformation of eggplant. However, other transformation techniques can be used, inasmuch as the advantages associated with the methods and compositions of the invention relate mainly to the tissue culture and regeneration of transformed tissue. Other plant transformation methods include biolistic delivery of the transforming DNA and delivery by electroporation, among others.

A preferred embodiment of the present invention comprises the following transformation/regeneration protocol, based on Agrobacterium-mediated transformation. Axenic leaf or stem tissue is excised and placed on SR medium for an optional preculturing period of up to one week. The purpose of this step, if used, is to allow acclimation of the explants to the medium and to wound the plants for better access of the Agrobacterium. Accordingly, the preculturing period should end prior to the formation of callus over the cut portions of the explants. The explants are then cocultivated with *A. tumefaciens* for a period of a few seconds (i.e. a short dip of the explant into a suspension of the bacteria) to a few days, the object being to inoculate the explants with the bacteria. After cocultivation, the explants are blotted and placed back on SR medium (without antibiotics) for a few hours to about two days, the object being to allow sufficient time for penetration of the tDNA into cells, but to avoid overgrowth of the culture with the Agrobacterium. The explants are then transferred to selection medium containing the selection antibiotic (e.g. kanamycin) and the antibiotic for removal of the Agrobacterium. Explants are kept on this medium for several weeks (e.g. 6–12 weeks) while shoot regeneration takes place. During this time they are transferred to fresh medium periodically, e.g. every 2–3 weeks. Explants with well-formed shoots are then transferred to another medium containing appropriate factors (e.g., zeatin instead of TDZ and 2iP), after which they are transferred to a potting mix for rooting. Such tissue culture methods and media are well known to persons skilled in the art of plant tissue culture. The aforementioned cultures generally are performed at about room temperature, e.g., 22–26° C., under a light regimen of between about 30 and 70 $\mu$mol/m²/sec.

A particularly preferred embodiment of the present invention comprises the following transformation and regeneration protocol: (1) axenic leaf tissue is excised and precultured for 48 h on SR medium; (2) leaf explants are cocultivated with *A. tumefaciens* for 1 min; (3) after blotting, tissue is cultured on SR medium for another 48 hours and then transferred to selection medium containing both 50 μg/mL kanamycin and 300 μg/mL augmentin. A transformation/regeneration efficiency of 20.8% has been observed for shoot production and over 400 putative transgenic plants have been produced with this method. From 50 putative transgenic plants, gene integration has been confirmed with Southern blot analysis and progeny tests.

The transformation/regeneration formulations and protocol of the present invention can be used to introduce any gene of interest into eggplant. Examples of useful genes include, but are not limited to genes encoding: (1) Bt toxin, as described in greater detail below; (2) bacterio-opsin (Mittler et al., 1995); (3) glucose oxidase (Wu et al., 1995); (4) delta-9 desaturase (Wang et al., in press); and (5) pokeweed antiviral protein (Lodge et al, 1995).

This invention provides transgenic eggplants produced by the above-described methods, and also is intended to encompass cells and tissues of those plants, including, but not limited to, leaves, stems, shoots, roots, flowers, fruits and seeds. In a preferred embodiment, seeds of the transgenic plants produced by the methods of the invention are provided.

The plants grown from the aforementioned seeds, or seeds from other eggplant varieties, or the progeny thereof, all of which are considered within the scope of this invention, are used in crosses and selection methods to transfer the gene of interest into other eggplant genotypes, cultivars, varieties and the like. For example, Italian varieties, white, variegated or purple, Black Jack, and others, are appropriate. Numerous traditional breeding techniques are known in the art of breeding eggplants. Through breeding and selection, a great variety of eggplants can be produced that carry and express a gene of interest.

Plants grown from the transgenic seeds of the invention can also be used to detect the presence of the inserted transgene and vector sequences using DNA extraction, cleavage by one or more restriction endonucleases, and analysis, e.g., Southern blotting using probes derived from the gene or genes of interest. In this manner, the transfer of foreign genes into progeny of breeding crosses can be monitored. An example of the use of such detection and monitoring methods is described in greater detail in Example 2.

In a preferred embodiment, this invention provides transgenic eggplants carrying the synthetic cryIIIA gene, which are highly resistant to the Colorado Potato Beetle. *Bacillus thuringiensis* var. *tenebriensis* is the source of the toxin gene modified into cryIIIA by Sutton et al., 1992. Herein we use the abbreviations Bt, Bt, Btt or Btt interchangeably to indicate the *B. thuringiensis* toxin gene or gene product.

Toxicity tests in planta and in vitro demonstrated that 69% of the cryIIIA-transformed plants generated by the aforementioned methods were resistant to neonate larvae and adult CPB. Transgenicity of the plants was confirmed by studies of GUS expression, Southern and northern analysis. Primary transformants, having a single insert of the construct, upon selfing, produced progenies co-segregating for the uidA and syn cryIIIA genes at the expected 3:1 ratios. The segregating resistant $R_1$ seedlings showed the same level of resistance as the parental genotypes, in growth chamber tests and under field conditions.

Transgenic eggplants having the cryIIIA gene were field tested in the presence of CPB and other pests. There was statistically significant resistance to CPB in each case. All parts of the plants show resistance to CPB, including fruit, flowers, leaves and stems. No negative effects were observed for plants expressing cryIIIA. For example, plant size, growth rate, fruit development and ripening were all normal.

Seeds of a preferred eggplant of the invention (i.e., transgenic and homozygous for a cryIIIA gene) have been produced from a preferred "Hibush" variety of *Solanum melongena* L., and are designated as genotype 55-30. Seeds of this genotype have been used to grow fertile CPB resistant plants.

As used herein, the term "resistant" or "resistance" means the ability of a plant to overcome, completely or to some degree, the detrimental effect of a pathogen or other damaging factor, such as an insect pest. In the instant case, the transgenic plants are resistant to certain insect pests by virtue of producing a Bt protein that is toxic to several kinds of insects (listed below). The Bt protein is sometimes referred to herein as "Bt toxin" or "Bt insecticidal protein", and refers to the major protein component of the parasporal crystals formed in strains of *B. thuringiensis*. This protein exhibits selective toxicity to different species of insects; those species are sometimes referred to herein as being "sensitive" to the protein.

Though the cryIIIA gene is exemplified herein, any other Bt gene modified for expression in plants can also be used in accordance with the present invention. Such genes include, but are not limited to, modified forms of the lepidopteran cryIA(b) and cryIA(c) Bt genes (Perlak et al., 1990; Perlak et al., 1991) and modified cryIA (Armstrong et al., 1995) and cryIC (Van der Salm et al., 1994).

Transgenic eggplants that carry and express the aforementioned Bt genes are expected to be highly resistant not only to the Colorado potato beetle, but also to other insects that are sensitive to Bt toxin. For instance, coleopteran insects that are sensitive to the Bt toxin produced by expression of the Btt gene of *B. tenebrionis* include Colorado potato beetle and elm leaf beetle. Lepidopteran insects sensitive to the Bt toxin produced by expression of the Btk gene of *B. kurstaki* include imported cabbage worm, cabbage looper, hornworm, European corn borer, cutworm, army worm, diamond back moth, spruce budworm, bag worm, tent caterpillar, gypsy moth, Indeanmean moth, corn earworm and coddling moth. Dipteran insects sensitive to the Bt toxin produced by expression of the Bti gene of *B. israelensis* include black fly, mosquito and fungus gnat. Lepidopteran insects sensitive to the Bt toxin produced by expression of the Bta gene of *B. aizawai* include wax moth, tobacco budworm, cotton bollworm and western grape skeletonizer.

The following examples are provided to describe the invention in greater detail. They are intended to illustrate, not to limit, the invention.

EXAMPLE 1

Effect of Growth Regulators and Antibiotics on Efficiency of Eggplant Transformation We have developed a reliable protocol for transformation and regeneration of eggplant explants in vitro. This example presents the main operational steps in this protocol and the most critical factors responsible for making the procedure an efficient one.

MATERIALS AND METHODS

Plant material/stock plants. Seeds of eggplant (*Solanum melongena* L. cv. Hibush) were surface-sterilized in 1.050% sodium hypochlorite and a few drops of Tween-20 for 20 min followed by five rinses (5 min each) with sterilized-distilled water and incubated overnight in a small film of sterile distilled water (10 mL); and then surface-sterilized a second time with 0.525% sodium hypochlorite for 15 min followed by three final rinses (5 min per rinse) with sterilized-distilled water. Seeds were cultured on ½ strength Murashige and Skoog (MS) (1962) basal salts and vitamins containing 2% sucrose and 0.6% agar (gum-agar, USB, Cleveland, Ohio). Stock plants were maintained by excising 2 cm of the shoot tip and sub-culturing them into glass jars containing 30 mL MS medium. Once shoots developed 6–8 vegetative leaves, leaves and internodal stem segments were excised and used for regeneration and transformation experiments.

Regeneration from leaf and stem explants. Leaf discs (3×8 mm) and stem segments (10 mm in length) were initially cultured on media used by other researchers for eggplant transformation and regeneration. All these media used MS basal salts and vitamins, 2% sucrose and 0.6% agar along with the following plant growth regulators: 10 $\mu$M zeatin (Guri and Sink, 1988), 5 $\mu$M zeatin (Rotino and Gleddie, 1990), and 5 and 10 $\mu$M BA along with either 0 or 1 $\mu$M 2,4-D (Gill, 1994). In addition, leaf discs were cultured on media containing 0, 0.01, 0.1, or 1.0 $\mu$M TDZ combined with 0, 5, 10, or 20 $\mu$M 2iP. After four weeks, numbers of bud primordia and shoots were recorded. Shoot regenerants were then transferred to shoot elongation media consisting of MS salts and vitamins, 2% sucrose, and 0.6% agar without growth regulators or with either 0.5 or 1.0 $\mu$M zeatin.

Bacteria and plasmids. Some of the plasmid constructs with the native cryIIIB gene used in these transformation experiments have been described recently (Chen et al., 1995). For these experiments, eight constructs were used which contained the coding region of the cryIIIB gene driven by the CaMV 35S and NOS regulatory elements (FIG. 1). PRU1 and pRU2 contained a 150 bp leader sequence while the remaining constructs contained an 8 bp leader sequence. PRU01, pRU02, pRU03, and pRU04 contained a translation enhancer (Gallie et al., 1987). PRU03 and pRUU04 contained double-35S promoters. In all odd numbered constructs, the Bt gene was inserted in the same orientation of flanking selective marker and reporter genes; while in even numbered constructs, the orientation was in the opposite direction. All constructs were inserted into the Hind III polylinker site of pBI121 (Clontech, Palo Alto, Calif.), and transferred into *A. tumefaciens* LBA4404 (Clontech). The new strains were consecutively identified as Q10, Q20, Q30, Q40, Q201, Q202, Q203, and Q204 ("Q series"). Bacterial cells were grown in YEB (Yeast extract-beef extract) medium (1 g yeast, 5 g beef extract, 5 g peptone, 5 g sucrose, 0.5 g $MgSO_4$, pH 7.2 in 1 L) containing 25 $\mu$g/mL kanamycin, at 28° C. and at 250 rpm for 48 h. Bacterial cells were pelleted and resuspended in liquid MS medium at its original titer (between 1–1.5 $OD_{600}$).

Plant transformation. Following the protocol of McCormick et al. (1986), leaf discs (3×8 mm) and stem explants (10 mm in length) were excised and placed on a shoot regeneration (SR) medium consisting of MS basal salts and vitamins, 10 $\mu$M 2iP, 0.1 $\mu$M TDZ, 2% sucrose, 0.6% agar, pH 5.8 for 48 h. Explants were inoculated for 1 min with one of the *A. tumefaciens* strains of the "Q series" (resuspended in liquid MS medium), blotted, and placed back onto the SR medium. After 48 h, the explants were blotted again and cultured on SR selection medium containing 300 $\mu$g/mL augmentin and 50 $\mu$g/mL kanamycin. Explants were cultured in petri plates (100×15 mm) at 24° C., 16 h photoperiod, under fluorescent lights with a photon flux of 50 $\mu$Mol/m$^2$/s, and subcultured every 2–3 weeks onto fresh selection medium. After 6–8 weeks larger petri plates (100× 25 mm) were used. Ten separate *A. tumefaciens* cocultivation experiments, with all eight strains, were conducted with a total 1250 leaf explants. Once small shoots (1 cm in length) were observed, these were subcultured onto an elongation medium consisting of MS basal salts and vitamins, 1 $\mu$M zeatin, 2% sucrose, 0.6% agar, and 300 $\mu$g/mL augmentin. After two weeks non-rooted shoots (3–4 cm in length) were dipped in 0.1% IBA (hormodin #1, Merck Chemicals, NJ), and then transferred to a 2 sphagnum peat:1 vermiculite (by volume) mix and placed under intermittent mist for 1–2 weeks to induce rooting.

Effect of antibiotics on regeneration. Leaf discs (3×8 mm) were cultured on SR medium containing the following antibiotics: 150 $\mu$g/mL augmentin (4 amoxicillin:1 clavulanic acid, SmithKline Beecham, Philadelphia, Pa.), 300 $\mu$g/mL augmentin, 250 $\mu$g/mL cefotaxime (Calbiochem, LaJolla, Calif.), 500 $\mu$g/mL cefotaxime, 250 $\mu$g/mL carbenicillin, or 500 $\mu$g/mL carbenicillin. Three plates of each treatment with 10 leaf discs per plate along with three plates with SR medium without any antibiotic were used. After 3 weeks, data on number of buds and shoots per explant were taken and observations on morphology and health of shoots were made. In a second experiment, leaf discs were co-cultivated with *Agrobacterium tumefaciens* LBA4404 containing pBI121 (Clontech) prepared as described above. After co-cultivation for 48 h explants were blotted and placed on plates containing the various antibiotics listed above, but also containing 50 $\mu$g/mL kanamycin. Two plates per treatment with 10 leaf discs per plate were used. For a period of three months, explants were subcultured every 2 weeks, and the used plates were immediately washed with 3 mL of sterile distilled water. A mL of bacterial slurry was removed and the bacterial titer determined by dilution and plating onto YEB medium containing 25 $\mu$g/mL kanamycin.

In a third experiment, the effect of kanamycin concentration on regeneration from co-cultivated plant material was investigated. Leaf discs were co-cultivated in *A. tumefaciens* containing pBI121 prepared as described above. After 48 h, the leaf discs were blotted and cultured on SR medium containing 10, 20, 30, 40, 50, 60, 70, 80, 90, and 100 $\mu$g/mL kanamycin along with 300 $\mu$g/mL augmentin. Control, non-inoculated explants were cultured on SR medium containing the same concentrations of kanamycin. Tissue was subcultured every two weeks. After eight weeks, number of putative transformed growing points (callus and/or buds) were counted. The number of GUS-positive plants was determined after 5 months.

Transgenic plant assays. Leaf tissue from shoots was assayed by the fluorogenic GUS assay (Jefferson, 1987). Both primary transgenic plants and R progenies were subjected to the GUS assay. Genomic DNA of putative transformed plants was extracted according to Junghans and Metzlaff (1990). Five to ten $\mu$g DNA was restricted with Eco RV and electrophoresed on a 0.9% agarose gel. The DNA was blotted onto a nylon membrane according to Sambrook et al. (1989). Prehybridization, hybridization, detection, and randomly primed DIG-labled probe preparation was carried out according to the Boehringer Mannheim Genius System (Indianapolis, Ind.). The DNA probe was a 1.2 Kb segment of the native cryIIIB gene random primed-labeled with digoxigenin-11-dUTP.

RESULTS AND DISCUSSION

Figure 2A:
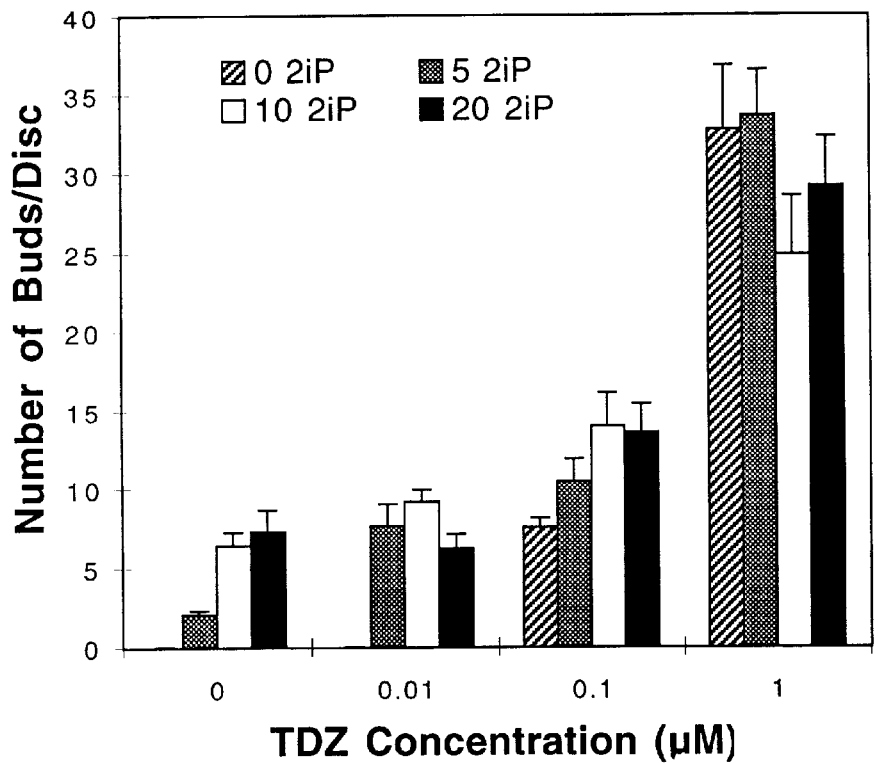
FIGS. 2A–2B. Combined TDZ and 2iP effect on bud (FIG. 2A) and shoot (FIG. 2B) regeneration from eggplant leaf discs.
Figure 2B:
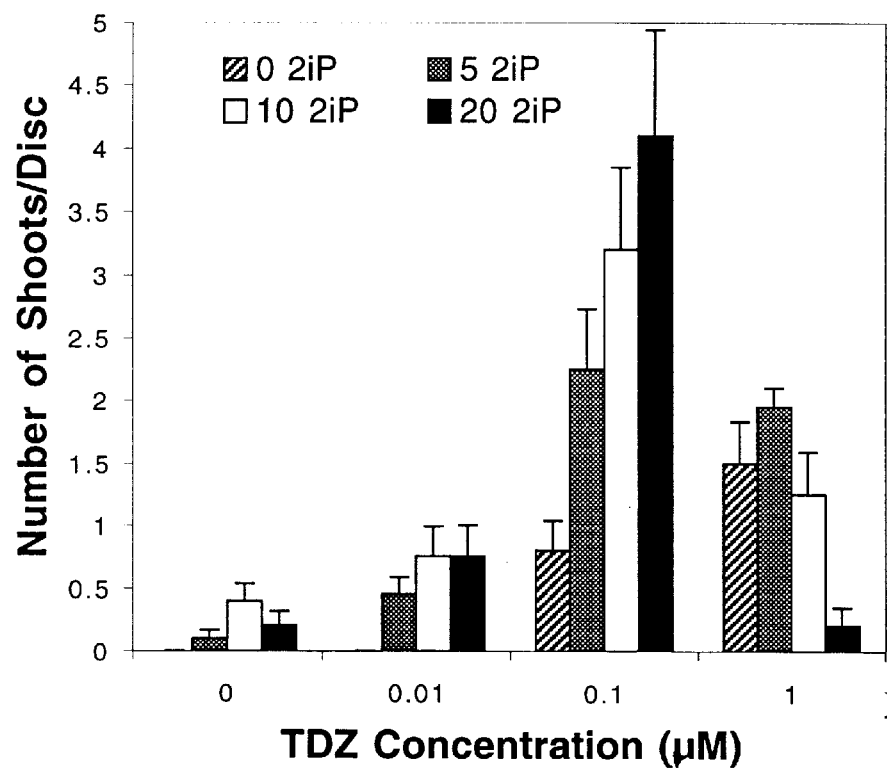

The effect of growth regulators on regeneration from leaf tissue. Leaf explants incubated on regeneration media containing 5–10 μM BA (Gill, 1994) developed mostly callus and a few vitrified shoots. Incorporation of 5 μM zeatin (Rotino and Gleddie, 1990) or 10 μM zeatin (Guri and Sink, 1989) into the medium resulted in the production of abundant callus on almost all the explants but only a few normal shoots were observed. In contrast, a high frequency of regeneration was observed on the media containing both TDZ and 2iP. After only two weeks in culture, numerous tiny, green buds could be seen along the cut edge of the explant tissue. A large number of these buds developed into shoots after four weeks in culture. Differences in production of callus, bud primordia and shoots were clearly seen between different treatments. Media containing 0 or 0.01 μM TDZ produced either callus only or callus with a few buds and shoots. It was observed that all media containing 1 μM TDZ, regardless of 2iP concentration, produced the highest number of bud primordia (FIG. 2A). Media which produced the highest number of shoots were 0.1 μM TDZ with either 10 or 20 μM 2iP (FIG. 2B). All bud primordia did not develop into shoots. Therefore, numbers of shoots/explant were lower than numbers of buds/explant. After four weeks the former medium had produced 13.9 bud primordia and 3.2 shoots per disc, the latter, 13.5 primordia and 4.1 shoots per disc. Twice as many buds formed on explants in media with 1.0 μM as those on 0.1 μM TDZ. However, over twice as many normal shoots were recovered from media which contained 0.1 μM TDZ. These results unequivocally indicated that TDZ was the critical component of these media in bud production. The optimal media for bud and shoot development contained 0.1 μM TDZ and either 10 μM 2iP or 20 μM 2iP. The former medium was selected for transformation studies and is referred to as the "shoot regeneration" (SR) medium. These results support previous observations that TDZ (thidiazuron) enhances shoot regeneration of other plant species (Fiola et al., 1990; Tsai et al., 1994; Szasz et al., 1995). Further development and elongation of 0.5–1.0 cm shoots was enhanced by the addition of 1.0 μM zeatin to MS medium. In general, leaf explants produced a higher number of shoots than stem explants. Out of 96 stem explants, only 46% regenerated normal shoots; whereas, all leaf explants regenerated multiple shoots. It was observed that the apical ends of stem segments regenerated buds and shoots, while the basal ends produced only friable callus.

Comparison of shoot development from controls and co-cultivated tissues. Differences in regeneration capacity were observed between control and inoculated explants. With control explants, shoots developed directly from explant tissue with little callus production. While, with co-cultivated explants, callus developed first along the cut surface, primarily along the mid-vein, from which buds differentiated and developed into normal shoots. With cocultivated explants cultured on kanamycin, it took 4–6 weeks for callus development, 7–11 weeks for bud differentiation, and 12–15 weeks for shoot development and elongation. Regeneration from control explants was observed two weeks following incubation, and unrooted plantlets were transferred to the greenhouse during the sixth week. Similar observations have been reported by Rotino and Gleddie (1990).

Effect of antibiotics on regeneration. Augmentin was used to eliminate Agrobacterium after cocultivation. Since most recent plant transformation protocols have used either carbenicillin or cefotaxime for this purpose and because augmentin has not been extensively used, its effects on regeneration were examined. Leaf discs cultured on SR medium containing 300 μg/mL augmentin induced high numbers of buds, usually clustered along the cut surface. Bud quality and the time it took to produce the buds was similar to those from control tissue cultured on SR medium without augmentin. However, the number of buds were significantly higher when the medium contained 300 μg/mL augmentin when compared to controls or media containing 500 μg/mL cefotaxime (Table 1).

TABLE 1

Effect of different antibiotics on shoot regeneration from eggplant leaf explants

| Antibiotic | Concentration (μg/mL) | Mean no.$^z$ ± SE | |
|---|---|---|---|
| | | Buds/explant | Shoots/explant |
| Augmentin | 300 | 36.6 ± 2.8 | 4.0 ± 0.3 |
| Control | 0 | 19.3 ± 1.7 | 3.9 ± 0.3 |
| Cefotaxime | 500 | 17.1 ± 1.3 | 2.5 ± 0.4 |

$^z$Fisher's protected LSD at P = 0.05 (n = 30)

Figure 3:
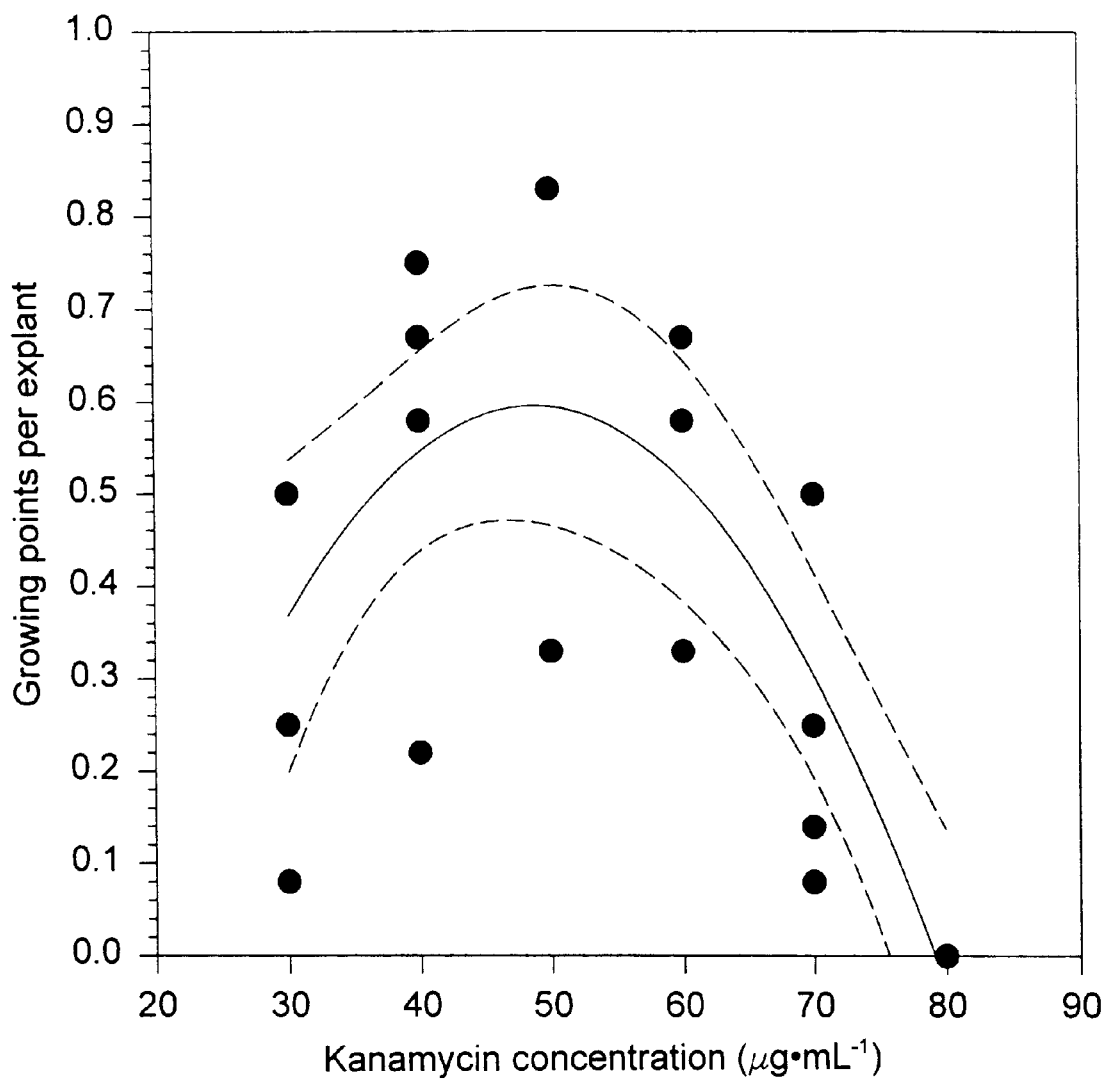
FIG. 3. Effect of kanamycin concentration on percent of cocultivated leaf discs to producing growing points after 2 months. Equations for lines were: Y=−0.95+0.06*Rate$_1$−0.0006*Rate$_2$, R$^2$=0.60.

Lower levels of augmentin (150 μg/mL) and cefotaxime (250 μg/mL) produced similar numbers of buds and shoots as their respective higher concentrations. Carbenicillin was almost as effective as augmentin in bud production, but it was only half as effective in shoot production (data not presented). Therefore, it is evident that augmentin produced no inhibitory effects on regeneration, and appears to enhance regeneration. augmentin (300 μg/mL) was extremely effective in eliminating Agrobacterium from the explants after three months, and it was similar to 500 μg/mL cefotaxime in this respect (data not presented). Carbenicillin at either concentration was not effective in elimination of Agrobacterium since a new burst of bacterial growth was observed after 8 weeks in culture, presumably due to the development of resistance to the antibiotic. Neither 150 μg/mL augmentin nor 250 μg/mL cefotaxime were effective in completely eliminating Agrobacterium. In our protocol, once shoots were transferred to the elongation medium and after three months of culture, augmentin was removed from the SR medium, and no bacterial growth was observed. Hibush cv. eggplant was found to be sensitive to kanamycin. No growth of any kind (swelling, callus, or buds) was observed with control non-inoculated leaf discs grown on 10–100 μg/mL kanamycin. However, once leaf explants were co-cocultivated with Agrobacterium, their ability to produce callus and buds in the presence of kanamycin increased. Regression analysis showed that the number of growing points (callus or buds) from cocultivated leaf discs significantly decreased at 70 μg/mL kanamycin after two months (FIG. 3). The number of transformed shoots was determined by GUS assay from the total population of regenerated and rooted shoots in the same experiment after 5 months. At relatively low concentrations of kanamycin, (30 or 40 μg/mL) 22% or 45% respectively of shoots tested positive for GUS activity. This was expected since selection of transformants was presumably not adequate at low concentrations which led to competition from "escapees". The highest percent (68) of GUS-positive shoots was obtained on medium containing 50 μg/ml kanamycin while regenerating explants on 60, 70 and 80 μg/ml produced 43, 0, and 0% GUS-positive plants respectively. Thus, at higher kanamycin concentrations, even transformed tissue failed to regenerate shoots. In almost all previously reported eggplant transformation experiments a high kanamycin concentration (100–200 μg/mL) was used to select for transformants (Guri and Sink, 1988; Filippone and Lurquin, 1989; Rotino and Gleddie, 1990; Fari et al., 1995). Our study showed that a lower kanamycin concentration was effective in selecting for transformants.

Figure 4:
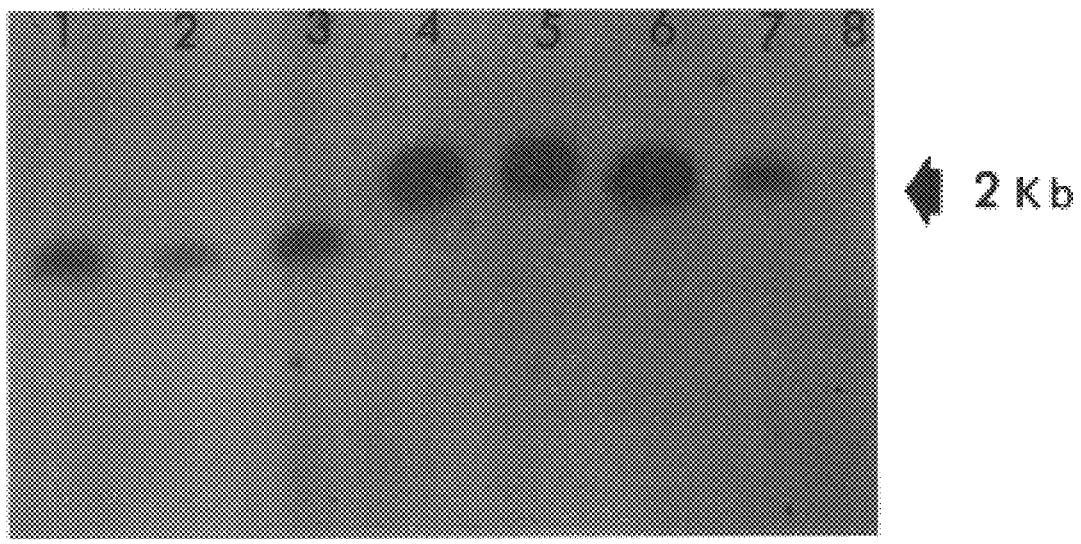
FIG. 4. Southern blot of eggplant DNA digested with Eco RV. The blots were probed with a 1.2 Kb DIG-labeled cryIIIB Bt gene. Washing and detection was according to the non-radioactive Genius system (Boehringer-Mannheim). DNA from putative transgenic and control plants as follows (T=transgenic plant): lane (1) T Q20; lane (2) T Q30; lane (3) T Q40; lane (4) T Q201; lane (5) T Q202; lane (6) T Q203; lane (7) T Q204; lane (8) control, not cocultivated plant.

Regeneration and transformation efficiency. Based on the above results, transformation was routinely carried out as follows: 1) axenic leaf tissue was excised and precultured for 48 h on SR medium; 2) leaf explants were cocultivated with A. tumefaciens for 1 min; 3) after blotting, tissue was cultured on SR medium for another 48 h and then transferred to selection medium containing both 50 μg/mL kanamycin and 300 μg/mL augmentin. There was considerable variability in percent explants producing callus and/or buds amongst different experiments. Regeneration efficiency, defined as percentage of explants producing growing points (callus or buds), varied between 20 to 63% with a mean of 38.8%. This may have been due to physiological and developmental conditions of leaflets at the time of explant excision which is an important factor in transformation efficiency (Van Wordragen and Dons, 1992). In addition, the titer of the bacterial culture might have influenced transformation (Lin et al., 1994). Shoots which emerged in the presence of kanamycin were screened for GUS. A total of 456 GUS-positive transformed plants from 10 different experiments were identified. Southern blot analysis conducted on 50 putative transgenic plants confirmed integration of the cryIIIB gene into the genomes (FIG. 4). Out of 305 GUS-positive plants from one of the experiments, 100 independent transformants have been identified from individual explants. In other words, some callus nodules produced multiple "sister" plants. In this protocol, transformation efficiency was defined as the number of independently transformed GUS-positive plants produced per number of cocultivated explants and it was 20.8% for this particular experiment. Integration of the cryIIIB gene was further verified by GUS analysis of S1 offspring from one of the primary transformants (S0). Out of 67 seedlings, 51 were GUS-positive and 16 GUS-negative. Thus the GUS gene was sexually transmitted as a dominant trait in a typical 3:1 Mendelian ratio.

EXAMPLE 2

Transformation of Eggplant with a Synthetic cryIIIA Gene to Produce a High Level of Resistance to the Colorado Potato Beetle This example describes the transformation of eggplant, using the methods of Example 1, with the synthetic cryIIIA gene from *Bacillus thuringiensis* var. *tenebriensis* (Btt) to produce plants resistant to CPB.

MATERIALS AND METHODS

Figure 5A:
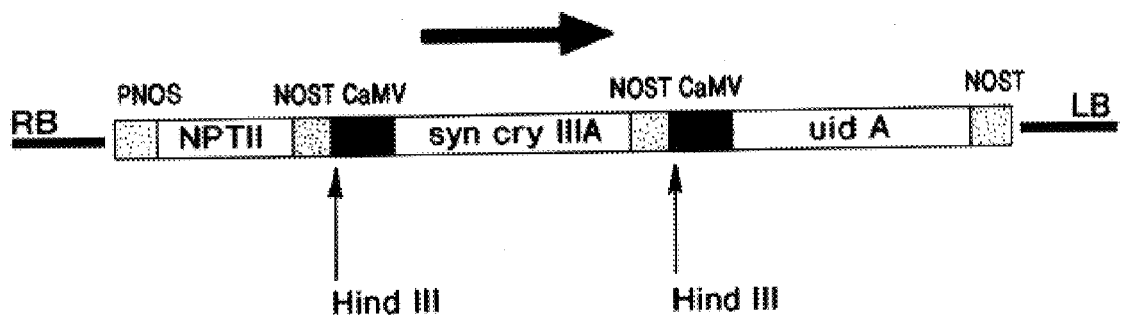
FIGS. 5A–5C. Structure of pSB1 construct and Southern blot analysis of primary transformants.

Engineering the chimeric syn cryIIIA construct. The coding sequence of the syn cryIIIA gene (Sutton et al., 1992) was excised by restriction with Bam HI and Kpn I from plasmid pSP73 (Promega) and, by blunt end ligation, inserted into the Pst I site of plasmid pCaMVCN (Pharmacia) with a deleted CAT gene. This insertion placed the coding sequence of the syn cryIIIA gene between the CaMV 35S promoter at its 5' terminus and the NOS terminator at its 3' terminus. Restriction with Hind III excised this chimeric fragment, which was then inserted at the Hind III site of pBI121 (Clontech, Palo Alto, Calif.), between the NPTII selectable and UidA reporter markers (FIG. 5A). This plasmid (pSB1) was transferred into *Agrobacterium tumefaciens* LBA4404 (Clontech) and used in the transformation of eggplant.

Transformation, regeneration, and transgenicity assay. Establishment of eggplant stock plants and the transformation and regeneration protocols from leaf segments were described in Example 1. Young leaves of putative transformed plants were assayed for GUS as described by Jefferson (1987).

Southern and northern blot analysis. Isolation of DNA and RNA, their electrophoresis and blotting were carried out as described previously (Chen et al., 1995). Two different probes were used in filter hybridization: a 1.8 Kb syn cryIIIA fragment excised from pSP73 with Kpn I and Bam HI; and a 1.8 Kb coding sequence of the GUS reporter gene restricted from pBI221 (Clontech, Palo Alto, Calif.) with Sst I and Xba I. The probes were DIG-labeled with the non-radioactive random-primed Genius™ method (Boeheringer Mannheim, Indianapolis Ind.). Hybridization and detection was carried out with the Genius™ method.

Western blot analysis. Protein was extracted by grinding 2 g of leaf tissue in liquid nitrogen and then resuspending in 4 ml extraction buffer as described (Koziel et al., 1993). After centrifugation, protein concentration in the supernatant was determined, and 100 μg of each sample was electrophoresed on a SDS denaturing gel. Electrophoresis and blotting was carried out according to Sambrook et al. (1989). The cryIIIA antibody was supplied to us by Ecogen (Philadelphia, Pa.) and detection and quantification of the protein was carried out with an Immun-blot assay (AP) kit from Bio Rad (Hercules, Calif.).

Toxicity test in planta. Vegetative propagules of the transgenic and control plants were planted in 6 inch pots and grown in a growth chamber with a photoperiod of 16 hours light (300 μmol/m$^2$/s at 27° C. and 8 hours dark at 22° C. When the plants reached the four to five leaf stage of growth and development, a CPB egg mass, with approximately 20–30 eggs, was placed on the basal leaf of each plant and fixed with a small dab of petroleum jelly. Hatching, development, and feeding of the larvae was checked on a daily basis. Resistance was determined by recording the mortality of the larvae and the stage of their development 10 days after hatching. The level of damage to leaves of individual eggplants after a period of ten days was assessed by visual evaluation. In addition, damage to transgenic plants from mature larvae and adult CPB, raised on control eggplants, was assessed. Feeding habits and viability of the insects on both transgenic and control eggplants was observed daily.

Toxicity test in vitro. One or two vigorously growing leaves of each plant were excised and the petiole was inserted into a piece of moist root cube and arranged in an insect rearing box. Ten first and/or second instar larvae of CPB were pre-weighed together and placed on a leaf in each of the insect rearing boxes. There were five replications for each plant genotype. After 6 days the larvae were weighed again. Mortality of the larvae was also recorded. Data was analyzed via ANOVA and means separation using the Ryan-Ernst-Gabriel-Welsch multiple F test (SAS, 1988).

Progeny tests. The primary transgenic plants ($R_0$) were selfed and seed of these plants were germinated in 2 sphagnum peat:1 vermiculite (by volume) mix in plastic grow cells under mist. After development of two primary leaves, the seedlings ($R_1$) were transplanted into three-inch (7 cm. sq.) pots and grown in the growth chamber. In a similar way, seedlings from non-transgenic plants were produced. The individual seedlings were tested for GUS activity and resistance to the CPB as described above (toxicity test in planta).

Heterozygous $S_1$ progeny from six primary transformants (Btt5, Btt16, Btt38, Btt55, Btt90, Btt204) were compared in the field with non-transgenic plants. Non transgenic controls were either: a) untreated; or b) treated with an insecticide imidacloprid (Admire 2F, Provado 1.6F - Bayer, Kansas City, Mo.) applied at 34.4 g [AI] per hectare as a pot drench in the greenhouse two weeks prior to planting and again on June 12 of the planting season, at 0.09 g [AI] per liter using a hand sprayer. All plants (240 plants per treatment) used in the study were seeded into 6" pots on April 9 of the planting season, grown under standard light, temperature, water and fertilization conditions in the greenhouse, and then hand transplanted into the field on May 30 of the same season.

produce a single band at the 2.5 Kb position, while the same digest, probed with uidA, was expected to produce different sizes and numbers of bands depending on the numbers of insertions (FIG. 5A). To verify transgenicity of the putative transformants, a total of 43 plants representing the four phenotypic categories described above were subjected to Southern analysis. Results are set forth in Table 2.

TABLE 2

Southern analysis of the four classes of transgenic eggplants.

| | Btt Probe | | | UidA Probe | | | | | | |
|---|---|---|---|---|---|---|---|---|---|---|
| | Number of plants | Results | | Number of plants | Results | | No. Inserts | | | |
| Phenotype | tested | + | − | tested | + | − | 0 | 1 | 2 | 3 | ≥4 |
| G+ R+ | 23 | 23 | — | 22 | 22 | — | — | 12 | 9 | 1 | — |
| G+ R− | 7 | 7 | — | 6 | 6 | — | — | 1 | 3 | 1 | 1 |
| G− R+ | 7 | 7 | — | 7 | 6 | 1 | 1 | 4 | 1 | | 1 |
| G− R− | 6 | 3 | 3 | 5 | 2 | 3 | 3 | — | 1 | — | 1 |

A randomized complete block design was used in the study. Each block consisted of 8 rows (one row per treatment) of 12 plants using a row spacing of 0.91 m between plants and 4.55 m between rows (total row length −10.8 m) and was replicated 20 times. To encourage the development of Colorado potato beetle populations in the study plot, eight rows of 'Superior' potatoes (two rows on each exterior border of the plot; four additional rows mid plot) were seeded five weeks prior to planting the eggplant transplants. Adult beetles, obtained from a colony maintained by the New Jersey Department of Agriculture's Phillip Alampi Biological Control Laboratory, were also released weekly into the potatoes between June 20–July 24.

Sampling of the different treatments was conducted weekly between June 27 and July 31. On each sample date, the total number of beetles (larvae and adults) and harvestable fruit was determined for each of the ten interior plants within a row and recorded. All data were transformed using √x+1 (Snedecor and Cochran 1967) and analyzed using analysis of variance (ANOVA) (SAS, 1988). Means for the total number of beetles and number of fruit per plant were separated by a least significant difference test (LSD).

RESULTS

Categorization of primary transformants. A total of 300 putative transformants were regenerated from the eggplant explants through tissue culture. When subjected to the GUS test, 185 tested positive (62%) and 115, negative (38%). Toxicity tests in planta with CPB were conducted on 146 GUS-positive, and 23 GUS-negative plants with the expectation that the latter could serve as negative controls. Results from these two tests revealed four phenotypically different categories of primary transformants: the majority (110 or 65%) were GUS-positive and CPB-resistant (G+R+); 36 (21%) were GUS-positive and CPB-susceptible (G+R−); seven (4%) were GUS-negative and CPB-resistant (G−R+); 16 (10%) were GUS-negative and CPB-susceptible (G−R−). Initially, the last two groups were considered to represent "escapees" which occurred during the transformation process but the CPB bioassays and Southern analysis revealed that most of the plants from this latter group were transformants.

Figure 5B:
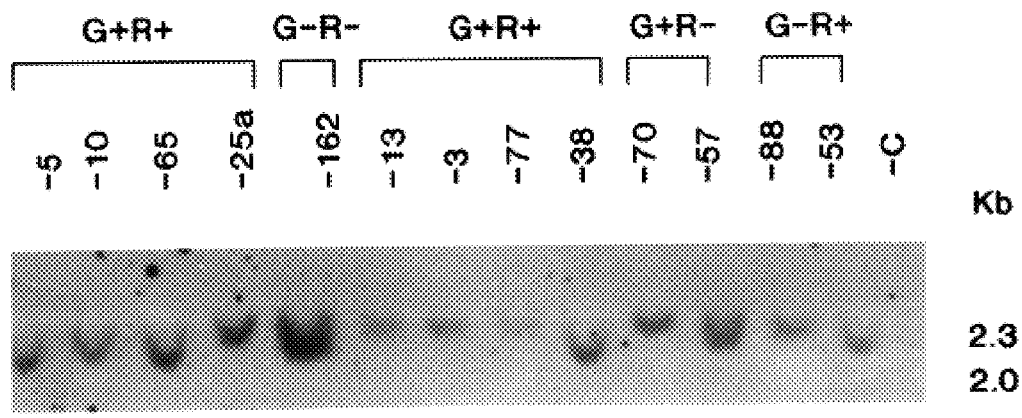
Figure 5C:
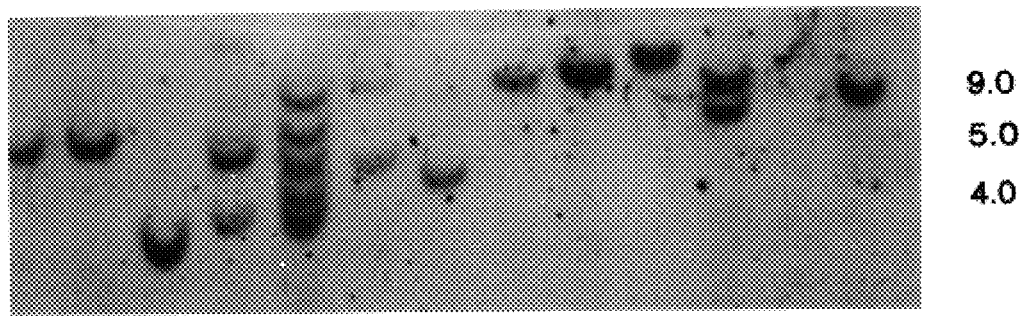

Southern analysis. A Hind III digest of DNA from transgenic plants, probed with syn cryIIIA, was expected to The cryIIIA gene was present in 40 out of 43 and the uidA in 36 out of 40 tested plants, proving transgenicity of the majority of these plants. A sample of the analyzed plants, displaying the Southern profiles for both syn cryIIIA and uidA, is shown in FIG. 5B and FIG. 5C. In the first category (G+R+) the phenotypic expression of both syn cryIIIA and uidA genes was directly correlated with their presence in the Southern blots (genotypes: Btt5, Btt10, Btt65, Btt25a, Btt13, Btt3, Btt77, Btt38). In the next two categories there was correlation of gene expression with either uidA (G+R−, genotypes Btt70 and Btt57) or cryIIIA (G−R+, genotype Btt53) while the corresponding linked gene, which had not been expressed, was also detected by Southern blot. An obvious exception was plant Btt88 in which the uidA gene had been deleted. In the fourth category (G−R−), three plants were found to harbor both genes which were not expressed (i.e., Genotype Btt162) and three plants that were actual escapees. The frequency of occurrence of transgenic plants containing various copies of the construct is shown in the right side of Table 2. As expected, the majority of transgenic plants (72%) harbor one or two insertions of the construct. Out of 17 plants with one majority of transgenic plants (72%) harbor one or two insertions of the construct. Out of 17 plants with one insertion, 70% expressed both genes; out of 14 plants with 2 insertions, 64% expressed both genes. Examples of the latter were genotypes Btt13 and Btt25a. Plants containing more than 3 insertions, such as genotype Btt162, did not express either of the genes. It was with Southern blot analysis, using the uidA probe, that clones which had originated from the same transformation event could be identified. One example is seen with genotypes Btt5 and Btt10, which were derived from the same leaf segment and had the same banding pattern. However, genotypes Btt25a and Btt162, which had also been derived from the same leaf segment, were determined to be individual transformants.

Figure 6A:
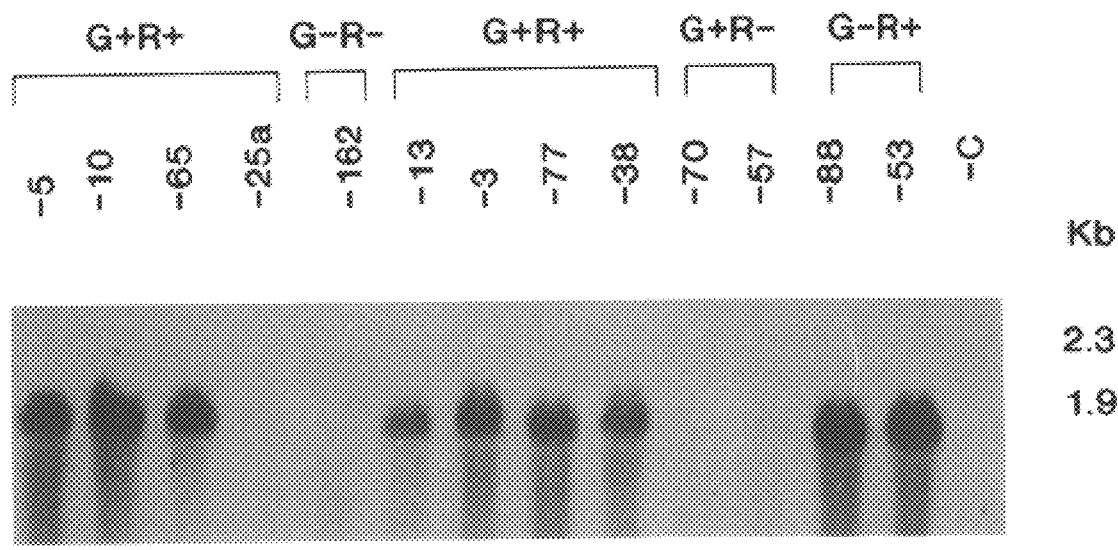
FIGS. 6A–6B. Northern analysis of total RNA from primary transformants.
Figure 6B:
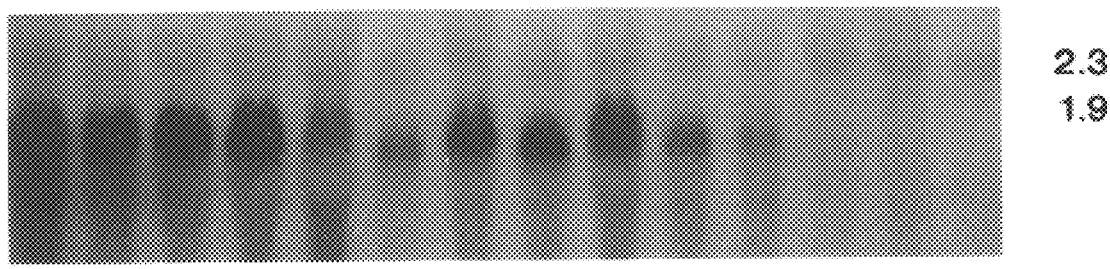
Figure 7A:
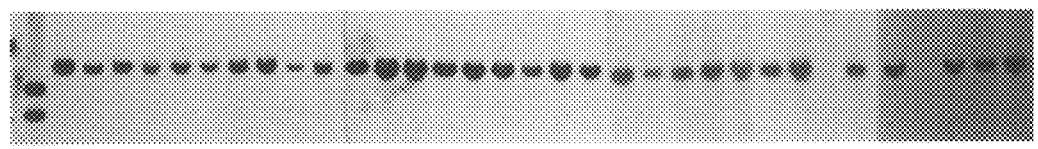
Figure 7B:
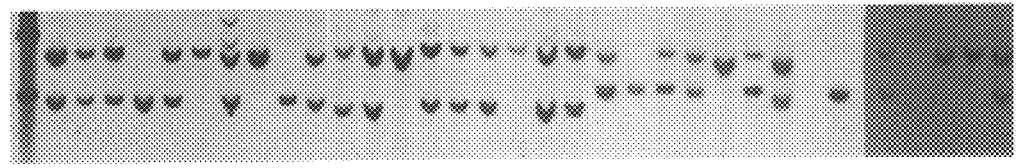
Figure 8:
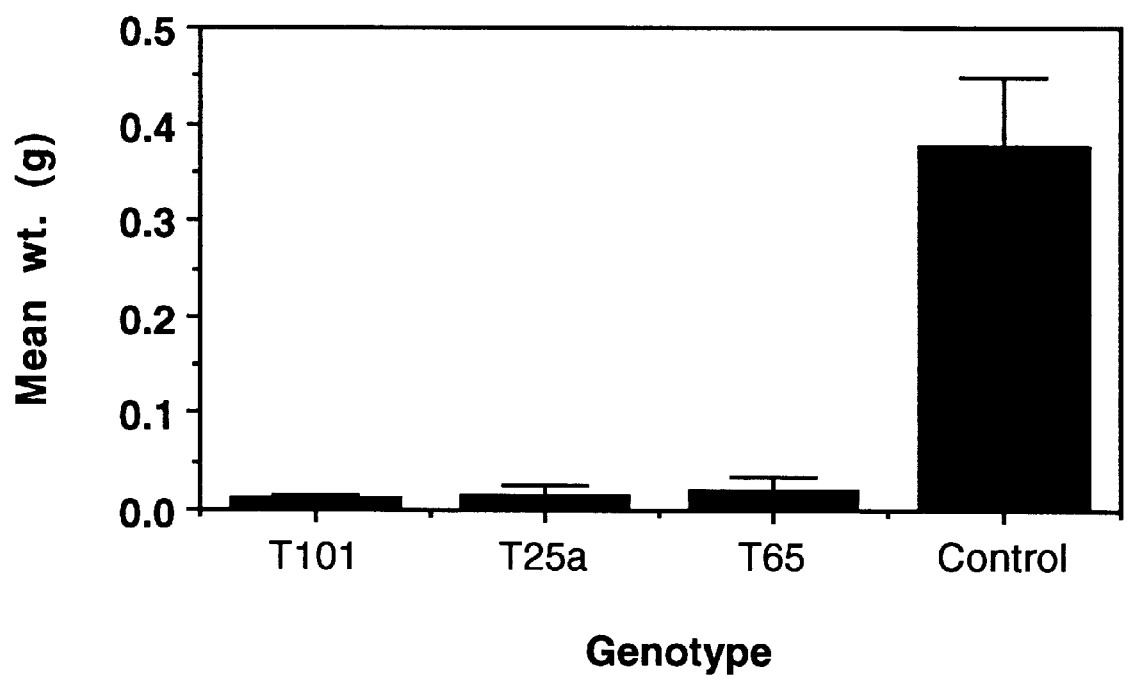
FIG. 8. Comparison of mean weight gain (gr.) of 10 larvae, 10 days after feeding on transgenic (T101, T25a, T65) or control plant leaves kept in insect rearing boxes.

RNA and protein analysis. To ascertain the expression of uidA and syn cryIIIA at the mRNA level, northern analysis of total RNA was performed (FIG. 6). As expected, a positive correlation was found between the phenotypic expression of the two genes (CPB resistance and GUS activity) and their expression at the mRNA level. Two genotypes were unusual: in Btt25a the Btt mRNA was not detected and yet the plant displayed resistance to CPB; in Btt162 the uidA mRNA was detected even though the GUS test had been negative. The cryIIIA protein was detected in variable amounts in all transgenic plants having a syn cryIIIA mRNA band (data not presented).

Progeny tests. The stability of incorporation of the syn cryIIIA and uidA genes in the primary transformants ($R_0$) was further assessed by studying their transmission and segregation pattern in $R_1$ generations. For this purpose 23 primary transformants, which were randomly selected, were self-pollinated and all except two produced seed. The two sterile transgenic plants were later found to have multiple copy numbers of the construct in their genomes. Eight primary transformants, consistently resistant to CPB, were selected for progeny analysis. Seven of these contained one insert and one contained two inserts (Btt25a). The results of this study are summarized in Table 3.

TABLE 3

Segregation analysis of GUS expression and CPB resistance (R = resistant, NR = non-resistant) in $R_1$ progenies of transgenic eggplants.

| Primary Transformants[z] | | No. | GUS Expres-sion | | | CPB Assay | | |
|---|---|---|---|---|---|---|---|---|
| Desig-nation | Pheno-types | Plants Tested | + | − | Calcu-lated[2] | R | NR | Calcu-lated[2] |
| 10 | G+ R+ | 32 | 24 | 8 | 0 | nt[y] | nt | |
| 16 | G+ R+ | 34 | 26 | 8 | 0 | 26 | 8 | 0 |
| 38 | G+ R+ | 36 | 31 | 5 | 1.81 | 31 | 5 | 1.81 |
| 55 | G+ R+ | 29 | 22 | 7 | 0.01 | 26 | 3 | 2.59 |
| 90 | G+ R+ | 36 | 23 | 13 | 1.81 | 24 | 12 | 0.93 |
| 204 | G+ R+ | 30 | 24 | 6 | 0.18 | nt | nt | |
| 53 | G− R+ | 30 | 12 | 18 | 17.78[x] | 5 | 25 | 51.37[x] |
| 25b | G+ R+ | 55 | 31 | 2 | 0.09 | 31 | 2 | 0.09 |

Figure 9:
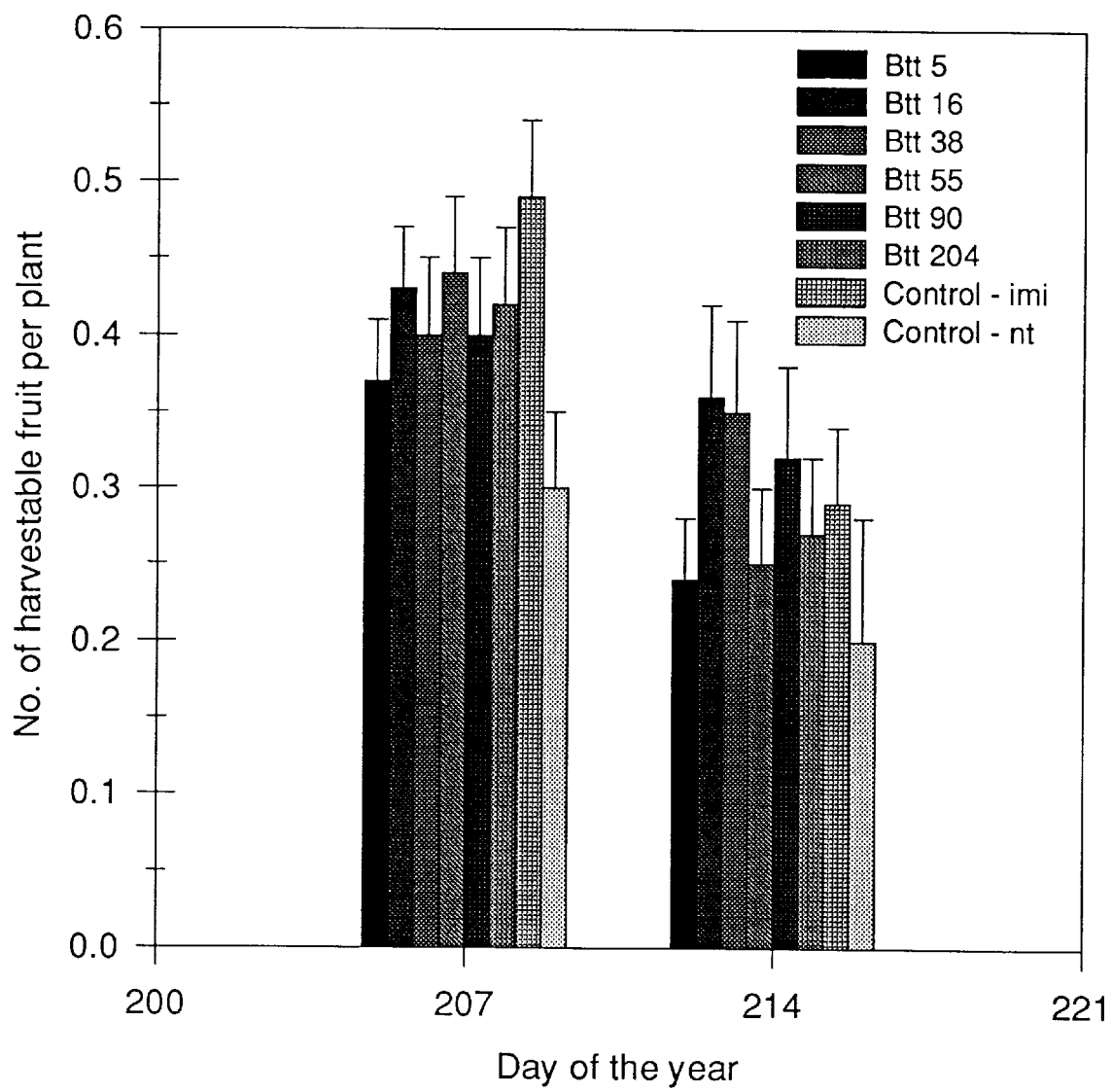
FIG. 9. Effect of Colorado potato beetles on the yield of transgenic (Btt5, Btt16, Btt38, Btt55, Btt90, Btt204) and non-transgenic (control-imi [imidacloprid- treated]; control-nt [not insecticide treated]) eggplant.

[z]The first seven progenies were tested for 3:1 and the last one for 15:1 segregation ratio
[y]nt = not tested
[x]Significant at <0.005 probability range Upon selfing, the first six plants in the table transmitted both genes to an expected proportion of their progeny for a dominant, single copy insert in the hemizygous transgenic plants. Regularity of the segregation for each gene in the $R_1$ generation is supported by low values of the calculated ($^2$). The co-segregational pattern of the uidA and syn cryIIIA genes reflect the contiguous position of these genes in the construct. In general, the seedlings showing GUS activity also displayed resistance to CPB. Discrepancy in co-segregation of the two genes in progenies of Btt55 and Btt90 is most likely due to seedling phenotype misclassification. The Btt53 genotype is unusual: although syn cryIIIA is expressed in the primary transformant ($R_0$), only a small proportion of the seedlings ($R_1$) displayed CPB resistance. In contrast, the uidA gene is not expressed in the primary transformant but about one half of the progeny showed GUS activity. In progenies of the Btt25a genotype high numbers of CPB-resistant and GUS-positive seedlings were obtained Since this genotype has two incorporated constructs, the ratio of 15:1, obtained from GUS analysis, for segregating duplicate hemizygous loci, indicates that the two inserts are on different homologous chromosomes. Progeny of genotype Btt25a were also analyzed for insert segregation at the DNA level (FIG. 7). Their pattern, when probed with the uidA fragment, followed a 9:3:3:1 ratio as indicated by the calculated ($^2$) value of 0.892. From the $R_1$ seedlings of genotypes Btt16 and Btt55 (G+R+), several homozygous genotypes have been isolated. All of their $R_2$ progenies were GUS-positive and will be used for future seed production and CPB-resistance studies in the field.

Toxicity assays. A single egg mass placed on the adaxial side of a leaf lamina produced 20–30 first instar larvae. On resistant transgenic plants the larvae spread over the lamina, eating small amounts of tissue, causing the formation of barely visible lesions. In some cases they even produced a few minute holes. In four to six hours after hatching, they became immobilized, ceased feeding, and in 15–20 hours appeared dead. The mortality of larvae was 100%, evidence of a high level of resistance. When adults or mature larvae were raised on the control plants and then transferred onto resistant transgenic plants, they initially consumed a noticeable amount of leaf tissue. However, after a few hours, their feeding became sporadic; they appeared less mobile and would languish for days in the same place on the leaf lamina. They died on the plants within 5–7 days. In contrast, the control plants were defoliated completely in less than a week by developing larvae. In a few primary transformants the resistance to CPB was assessed by following the growth rate and survival of the second-instar larvae on detached leaves. The weight of larvae raised on control plants was significantly higher than that of larvae raised on transgenic leaves (FIG. 8). As in the in planta tests, larval growth was arrested very early in development, and none survived after feeding on the Btt transgenic leaves.

The primary transformants, characterized as resistant to CPB by either test above, were field-planted in order to assess their resistance under conditions of natural infestation with CPB. Individual plants were rated for their general vigor and the severity of damage by CPB. Those plants with the best ratings were selected as parents for $S_1$ progenies which were evaluated for their horticultural values and particularly their resistance to CPB in a replicated trial, under field conditions. This showed that field populations of Colorado potato beetle (adults and larvae) were affected by the progenies tested (Table 4).

TABLE 4

Effect of transgenic and non-transgenic eggplant on Colorado potato beetle densities. Number of Colorado potato beetles per plant[z]

| Treatment | 27-June | 3-July | 10-July | 17-July | 24-July | 31-July |
|---|---|---|---|---|---|---|
| Btt5 | 9.75 | 6.02 | 1.45 | 0.82 | 0.48 | 0.24 |
| | b | cd | c | c | bcd | bc |
| Btt16 | 6.15 | 5.01 | 1.98 | 1.00 | 0.30 | 0.31 |
| | bc | d | b | bcd | cd | b |
| Btt38 | 4.50 | 11.94 | 2.18 | 0.88 | 0.90 | 0.34 |
| | bc | a | b | bc | a | b |
| Btt55 | 7.70 | 5.19 | 1.98 | 1.08 | 0.33 | 0.56 |
| | bc | d | b | bc | bcd | a |
| Btt90 | 6.15 | 8.96 | 1.94 | 0.70 | 0.17 | 0.15 |
| | c | ab | b | d | d | c |
| Btt204 | 3.80 | 7.44 | 2.08 | 1.08 | 0.48 | 0.28 |
| | c | bc | b | bcd | bc | bc |
| control-imi[y] | 1.65 | 6.26 | 3.24 | 1.17 | 0.47 | 0.65 |
| | d | cd | a | b | abc | a |
| control-nt[x] | 14.75 | 10.03 | 4.25 | 1.75 | 0.66 | 0.58 |
| | a | a | a | a | ab | a |

[z]Means within a column followed by the same letter are not significantly different at the P ≦ 0.05 level (LSD); n = 200.
[y]control-imi = nontransgenic plants, treated with insecticide imidacloprid
[x]control-nt = nontransgenic plants, not treated with insecticide Throughout the study significantly fewer beetles (P≦0.05) were observed on the transgenic progenies when compared to untreated non-transgenic plants. In addition, on most sample dates, significantly fewer beetles (P≦0.05) were found on the transgenic plants than on control plants treated with imidacloprid. Overall, there were small differences amongst tested transgenic progenies in resistance to CPB. This resistance was manifested in higher numbers of fruit per plant in the heterozygous transgenic population in comparison to non treated controls (FIG. 9). These results indicate that a commercial eggplant variety, developed from the homozygous derivatives of the resistant seedlings, would provide a viable alternative to the control of CPB.

DISCUSSION

A population of primary transgenic eggplants carrying the syn cryIIIA gene displayed resistance to CPB in 69% of the primary transformants. The biotoxicity assays of the resistant plants have demonstrated conclusively that the syn cryIIIA gene is expressed at a level which is toxic to the first or second instar larvae of CPB. The effect of the toxic protein is swift and consistent: 1) on the leaves of transgenic plants, all the neonate larvae die within a few hours after hatching; 2) the adult insects, raised on non-transgenic genotypes and transferred onto transgenic leaves languished within 8–10 days, causing minor damage to various plant parts on different transgenic plants before they die. The segregating $R_1$ resistant seedlings, tested in the growth chamber, showed similar levels and patterns of resistance under field conditions. This demonstrates that the observed resistance in the growth chamber tests, with laboratory-derived strains of CPB, reflected the sensitivity of the general, natural CPB population to the syn cryIIIA gene. The level of resistance in the studied progeny is adequate for controlling CPB under commercial conditions. It should be noted that from the field-tested progeny, a small proportion were non-resistant segregants. However, the average survival of larvae and adult insects was still lower than in control seedlings. Homozygous non-segregating genotypes isolated from the $S_1$ generation are presently being tested under field conditions, with the expectation that the level of resistance in these transgenic seedlings will be increased. A logical follow-up to these studies is to select the most suitable (resistant) genotype for development of a management strategy, under commercial conditions, that would deter development of insect tolerance or resistance to the syn cryIIIA gene product (Mallet and Porter, 1992). Most importantly, it is clear that the expression of syn cryIIIA gene is higher than the previously tested native cryIIIB gene in transgenic eggplant (Chen et al., 1995). Those results are in agreement with the expression of the same gene in tobacco and potato, and other modified cryI genes incorporated into various plant species (Van der Salm et al., 1994; Armstrong et al., 1995; Wunn et al., 1996). The chimeric construct was found to be incorporated stably in all the transgenic plants studied and was transmitted through the sexual process in a regular manner, leading to Mendelian segregation ratios in all but one genotype (Btt53).

REFERENCES

Adang, M. J., M. S Brody, G. Cardineau, N. Eagan, R. T. Roush, C. K. Shewmaker, A. Jones, J. V. Oakes, and K. E. McBride. 1993. The reconstruction and expression of a *Bacillus thuringiensis* cryIIIA gene in protoplasts and potato plants. Plant Mol. Biol. 21:1131–1145.

Armstrong, C. L., G. B. Parker, J. C. Pershing, S. M. Brown, P. R. Sanders, D. R. Duncan, T. Stone, D. A. Dean, D. L. DeBoer, J. Hart, A. R. Howe, F. M. Morrish, M. E. Pajeau, W. L. Petersen, B. J. Reich, R. Rodriguez, C. G. Santino, S. J. Sato, W. Schuler, S. R. Sims, S. Stehling, L. J. Tarochione, and M. E. Fromm. 1995. Field evaluation of European corn borer control in progeny of 173 transgenic corn events expressing an insecticidal protein from *Bacillus thuringiensis*. Crop Sci. 35:550–557.

Chen, Q., G. Jelenkovic, C-K Chin, S. Billings, J. Eberhardt, J. Goffreda, and P. Day. 1995. Transfer and transcriptional expression of coleopteran cryIIIB endotoxin gene of *Bacillus thuringiensis* in eggplant. J. Am. Soc. Hort. Sci. 120:921–927.

Fari, M., Nagy, I., Marta, C., Mityko, J. and A. Andrasfalvy. 1995. Agrobacterium mediated genetic transformation and plant regeneration via organogenesis and somatic embryogenesis from cotyledon leaves in eggplant (*Solanum melongena* L. cv. 'Kecskemeti lila'). Plant Cell Rep. 15:82–86.

Filippone, E. and P. F. Lurquin. 1989. Stable transformation of eggplant (*Solanum melongena* L.) by cocultivation of tissues with *Agrobacterium tumefaciens* carrying a binary plasmid vector. Plant Cell Rep. 8:370–373.

Fiola, J. A., Hassan, M. A., Swartz, H. J., Bors, R. H. and R. McNicols. 1990. Effect of thidiazuron, light fluence rates and kanamycin on in vitro shoot organogenesis from excised Rubus cotyledons and leaves. Plant Cell. Tiss. Org. Cult. 20:223–228.

Gallie, D. R., Sleat, D. E., Watts, J. W., Turner, P. C., and M. A. Wilson. 1987. The 5(-leader sequence of tobacco mosaic virus RNA enhances the expression of foreign gene transcripts in vitro and in vivo. Nucl. Acids Res. 15:3257–3273.

Gill, J. M. 1994. Transformation of eggplant (*Solanum melongena* L.) and chinese kale (*Brassica alboglabra* Bayley) using *A. tumefaciens* as a vector. Cook College, Rutgers University, NJ, Ph.D. Thesis.

Guri, A. and K. C. Sink. 1988. Agrobacterium Transformation of Eggplant. J. Plant Physiol. 133:52–55.

Jefferson, R. A. 1987. Assaying chimeric genes in plants: the GUS gene fusion system. Plant Mol. Biol. Rptr. 5:387–405.

Junghans, H. and M. Metzlaff. 1990. A simple method for the preparation of total plant DNA. Biotech. 8:176.

Koziel, M. G., G. L Beland, C. Bowman, N. B. Carozzi, R. Crenshaw, L. Crossland, J. Dawson, N. Desai, M. Hill, S. Kadwell, K. Launis, K. Lewis, D. Maddox, K. McPherson, M. Meghji, E. Merlin, R. Rhodes, G. Warren, M. Wright, and S. V. Evola. 1993. Field Performance of Elite Transgenic Maize Plants Expressing an Insecticidal Protein Derived from *Bacillus thuringiensis*. Bio/Tech. 11:194–200.

Lin, J-J., Assad-Garcia, N. and J. Kuo. 1994. Effects of Agrobacterium Cell Concentration on the Transformation Efficiency of Tobacco and *Arabidopsis thaliana*. Focus: Life Technologies 16(3):72–22.

Lodge, J. K., K. Wojciech and N. Turner. 1995. Broad-Spectrum Virus Resistance in Transgenic Plants Expressing Pokeweed Antiviral Protein. Proc. Natl. Acad. Sci. USA 90:7089–7093.

Mallet, J. and P. Porter. 1992. Preventing insect adaptation to insect-resistant crops: are seed mixtures or refugia the best strategy? Proc. Royal Soc. London B. 250:165–169.

Matzke, M. and A. Matzke. 1993. Genomic Imprinting in Plants: Parental Effects and Trans-Inactivation Phenomena. Annu. Rev. Plant Physiol. Plant Mol. Biol. 44:53–76.

McCormick, S., Niedermeyer, J., Fry, J., Barnason, A., Horsch, R., and R. Fraley. 1986. Leaf disc transformation of cultivated tomato (*L. esculentum*) using *A. tumefaciens*. Plant Cell Rep. 5:81–84.

Mittler, R., V. Shulaev and E. Lam. 1995. Coordinated Activation of Programmed Cell Death and Defense Mechanisms in Transgenic Tobacco Plants Expressing a Bacterial Proton Pump. Plant Cell 7:29–42.

Murashige, T. and F. Skoog. 1962. A revised medium for rapid growth and bioassays with tobacco tissue cultures. Physiol. Plant. 15:473–497.

Murray, E. E., T. Rocheleau, M. Eberle, C. Stock, V. Sekar, and M. Adang. 1991. Analysis of unstable RNA transcripts of insecticidal crystal protein genes of *Bacillus thuringiensis* in transgenic plants and electroporated protoplasts. Plant Mol. Biol. 16:1035–1050.

Perlak, F. J., R. W. Deaton, T. A. Armstrong, R. L Fuchs, S. R. Sims, J. T. Greenplate, and D. A. Fischhoff. 1990. Insect resistant cotton plants. Bio/Tech. 8:939–943.

Perlak, F. J., R. L. Fuchs, D. A. Dean, S. L. McPherson, and D. A. Fischhoff. 1991. Modification of the coding sequence enhances plant expression of insect control protein genes. Proc. Natl. Acad. Sci. USA 88:3324–3328.

Rotino, G. L. and S. Gleddie. 1990. Transformation of eggplant (*Solanum melongena* L.) using a binary *Agrobacterium tumefaciens* vector. Plant Cell Rep. 9:26–29.

Sambrook, J., T. Maniatis and E. F. Fritsch. 1989. Molecular cloning: A laboratory manual. 3rd ed. Cold Spring Harbor Laboratory Press.

SAS Institute Inc. SAS/STAT( User's Guide, Release 6.03 Edition. Cary, NC:SAS Institute Inc., 1988. 1028 pp.

Snedecor, G. W., and W. G. Cochran. 1978. Statistical Methods. Iowa State University Press, Ames, Iowa, 593 pp.

Sutton, D. W., P. K. Havstad, and J. D. Kemp. 1992. Synthetic cryIIIA gene from *Bacillus thuringiensis* improved for high expression in plants. Transgenic Res. 1:228–236.

Szasz, A., Nervo, G., and M. Fari. 1995. Screening for in vitro shoot-forming capacity of seedling explants in bell pepper (*Capsicum annuum* L.) genotypes and efficient plant regeneration using thidiazuron. Plant Cell Rep. 14:666–669.

Tsai, C-J., Podila, G. K., and G. K. Podila. 1994. Agrobacterium-mediated transformation of quaking aspen (*Populus tremuloides*) and regeneration of transgenic plants. Plant Cell Rep. 14:94–97.

Van Aarssen, R., P. Soetaert, M. Stam, J. Dockx, V. Gossele, J. Seurinck, A. Reynaerts, and M. Cornelissen. 1995. CryIA(b) transcript formation in tobacco is inefficient. Plant Mol. Biol. 28:513–524.

Van der Salm, T., D. Bosch, G. Honee, L. Feng, E. Munsterman, P. Bakker, , W. J. Stiekema, and B. Visser. 1994. Insect resistance of transgenic plants that express modified *Bacillus thuringiensis* cryIA(b) and cryIC genes: a resistance management strategy. Plant Mol. Biol. 26:51–59.

Van Wordragen, M. F. and H. J. M. Dons. 1992. *Agrobacterium tumefaciens*-mediated transformation of recalcitrant crops. Plant Mol. Biol. Rep. 10:12–36.

Wang, C., C.-K. Chin and A. Chen. In Press. Expression of the Yeast Delta-9 Desaturase Gene in Tomato Enhances its Resistance to Powdery Mildew. Physiological and Molecular Plant Pathology.

Wu, G., B. Short, E. Lawrence, E. Levine, K. Fitzsimmons and D. Shah. 1995. Disease Resistance Conferred by Expression of a Gene Encoding $H_2O_2$-Generating Glucose Oxidase in Transgenic Potato Plants. The plant Cell 7:1357–1368.

Wunn, J., A. Kloti, P. K. Burkhardt, G. C. G. Biswas, K. Launis, V. A. Iglesias, and I. Potrykus. 1996. Transgenic indica rice breeding line IR58 expressing a synthetic cryIA (b) gene from *Bacillus thuringiensis* provides effective insect pest control. Bio/Tech. 14:171–176.

The present invention is not limited to the embodiments described and exemplified above, but is capable of variation and modification without departure from the scope of the appended claims.

What is claimed is:

1. A transgenic eggplant plant comprising a *Bacillus thuringiensis* cryIIIA gene having SEQ ID NO:1, the gene producing an amount of its encoded Bt insecticidal protein sufficient to render the eggplant plant resistant to Colorado potato beetle.

2. The transgenic eggplant of claim 1 which is *Solanum melongena* L. cv. Hibush.

3. Seeds of the transgenic eggplant of claim 1.

* * * * *